United States Patent
Zhan et al.

(10) Patent No.: US 6,934,024 B2
(45) Date of Patent: Aug. 23, 2005

(54) ELLIPSOMETRY METHODS AND APPARATUS USING SOLID IMMERSION TUNNELING

(75) Inventors: Qiwen Zhan, Centerville, OH (US); James R. Leger, Plymouth, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 159 days.

(21) Appl. No.: 10/388,857

(22) Filed: Mar. 14, 2003

(65) Prior Publication Data

US 2003/0227623 A1 Dec. 11, 2003
US 2004/0189992 A9 Dec. 11, 2003

Related U.S. Application Data

(63) Continuation-in-part of application No. 09/691,346, filed on Oct. 18, 2000, now Pat. No. 6,693,711.
(60) Provisional application No. 60/364,475, filed on Mar. 15, 2002.

(51) Int. Cl.[7] ................................................. G01J 4/00
(52) U.S. Cl. ....................................................... 356/369
(58) Field of Search ................................ 356/364–369, 356/370, 381–382; 250/372, 225

(56) References Cited

U.S. PATENT DOCUMENTS

| | | | | |
|---|---|---|---|---|
| 3,873,209 A | * | 3/1975 | Schinke et al. | ............. 356/135 |
| 4,508,832 A | * | 4/1985 | Carter et al. | ................. 436/517 |
| 4,893,932 A | * | 1/1990 | Knollenberg | ............... 356/369 |
| 5,022,743 A | | 6/1991 | Kino et al. | |
| 5,042,951 A | | 8/1991 | Gold et al. | |
| 5,108,185 A | * | 4/1992 | Mansuripur et al. | ........ 356/369 |
| 5,133,601 A | | 7/1992 | Cohen et al. | |
| 5,159,412 A | | 10/1992 | Willenborg et al. | |
| 5,181,080 A | | 1/1993 | Fanton et al. | |
| 5,204,734 A | | 4/1993 | Cohen et al. | |
| 5,220,403 A | * | 6/1993 | Batchelder et al. | ......... 356/450 |
| 5,359,622 A | | 10/1994 | Shih | |
| 5,486,701 A | | 1/1996 | Norton et al. | |
| 5,521,705 A | | 5/1996 | Oldenbourg et al. | |
| 5,602,643 A | | 2/1997 | Barrett | |
| 5,602,820 A | | 2/1997 | Wickramasinghe et al. | |
| 5,754,296 A | | 5/1998 | Law | |
| 5,822,973 A | * | 10/1998 | Kaneko et al. | ................ 57/206 |
| 5,910,841 A | | 6/1999 | Masao | |
| 5,939,709 A | * | 8/1999 | Ghislain et al. | ............ 250/216 |
| 5,963,326 A | | 10/1999 | Masao | |
| 5,991,488 A | * | 11/1999 | Salamon et al. | ............ 385/129 |
| 6,008,892 A | | 12/1999 | Kain et al. | |
| 6,127,183 A | * | 10/2000 | Ivarsson et al. | ............... 436/34 |
| 6,177,990 B1 | | 1/2001 | Kain et al. | |
| 6,404,544 B1 | | 6/2002 | Kuhn | |
| 6,421,128 B1 | * | 7/2002 | Salamon et al. | ............ 356/445 |
| 6,493,097 B1 | * | 12/2002 | Ivarsson | ..................... 356/630 |
| 6,594,011 B1 | * | 7/2003 | Kempen | ..................... 356/369 |

OTHER PUBLICATIONS

"Control of the Bias Tilt Angles in Nematic Liquid Crystals", Yablonsklii et al., J. Appl. Physics, vol. 85, No. 5 (Mar. 1, 1999).*
"Propagation Length of Guided Waves in Lossy Si Film Sandwiched by Identical Dielectrics," Takabayashi et al., J. Opt. Soc. Am B, vol. 12 No. 12, (Dec. 1995).*

(Continued)

*Primary Examiner*—Michael P. Stafira
(74) *Attorney, Agent, or Firm*—Mueting, Raasch & Gebhardt, P.A.

(57) ABSTRACT

A solid immersion tunneling ellipsometer and methods relating thereto may include a solid immersion apparatus (e.g., a prism or an objective lens in combination with a solid immersion lens) that facilitates optical tunneling and provide information that can be used in the determination of one or more characteristics (e.g., thickness, index of refraction, etc.) of samples (e.g., thin films, ultrathin films, etc.).

31 Claims, 13 Drawing Sheets

OTHER PUBLICATIONS

"Ellipsometry of Guided Wave Polarizations at Solid Surfaces", Burshta et al., Surface Science 301, (1994).*

"Molecular Orientation Near the Surface of a Smetic Liquid Crystal Cell Showing V–shaped Switching by Means of Attenuated Total Internal Reflection Ellipsometry", Ikeda et al., Phys. Rev. E vol. 63, (2001).*

"Imaging Surface Plasmon Resonance Sensor Based On Multiple Wavelengths: Sensitivity Considerations", Johansen et al., Rev. of Scien. Instrum., vol. 71, No. 9, (Sep. 2000).*

"Determination of Mid–IR Optical Constants of Water and Lubricants Using IR Ellipsometry Combined With an ATR Cell", Tiwald et al., Thin Solid Film, 313–314 (1998).*

"Ultra–thin SiO2 Film Studies: Index, Thickness Roughness and the Initial Oxidation Regime", Irene, Solid State Electronics 45 (2001).*

Pulsed Multiwavelength Laser Ranging System for Measuring Atmospheric Delay: Erratum, Moy, Appl. Optics vol. 20, No. 22 (Nov. 15, 1981).*

Zhan et al., "High–resolution imaging ellipsometer," *Applied Optics*, 2002; 41(22):4443–4450.

Zhan et al., "Near–field nano–ellipsometer for ultrathin film characterization,"*Journal of Microscopy*, 2003;210:214–219.

Zhan, "Novel Polarization Measurement and Manipulation Techniques for Nanometer Scale Applications," Thesis, University of Minnesota, Aug. 2002, 12 pgs.

Zhan, "Radiation forces on a dielectric sphere produced by highly focused cylindrical vectors beams," *J. Opt. A: Pure Appl. Opt.*, 2003;5;229–232.

Absolute Ellipsometry (AE). Therma–Wave Measurement Technologies [retrieved from the Iternet on Feb. 11, 2003]. http://thermawave.com/technology/ae.htm., 1 page.

Albersdorfer et al., "High resolution imaging microellipsometry of soft surfaces at 3μm lateral and 5 Å normal resolution", *Appl. Phys. Lett.*, 1998; 72(23):2930–2932.

Ashkin, "History of Optical Trapping and Manipulation of Small–Neutral Particle, Atoms and Molecules," *IEEE Journal on Selected Topics in Quantum Electronics*, 2000; 6(6):841–856.

Azzam et al., "Ellipsometry and Polarized Light", Amsterdam, North Holland Physics Publishing; 1988.

Beam Profile Ellipsometry (BPE). Therma–wave [retrieved on Jan. 15, 2001]. Retrieved from the Internet: <URL: http://www.thermawave.com/technology/bpe.htm>, 1 page.

Beijerbergen et al., "Helical–wavefront laser beams produced with a spiral phaseplate," *Optics Comm.*, 1994; 112:321–327.

Berger et al., "Resolution in surface plasmon microscopy," *Rev. Sci. Instrum.*, 1994; 65:2829–2836.

Biss et al., "Cylindrical vector beam focusing through a dielectric interface," *Optics Express*, 2001, 9(10):490–497.

Chou et al., "Subwavelength amorphous silicon transmission gratings and applications in polarizers and waveplates", *Appl. Phys. Lett.*, 1995; 67(6):742–744.

Cohn et al., "Dynamic imaging microellipsometry: theory, system design, and feasibility demonstration", *Applied Optics*, 1988; 27(22):4664–4671.

Courtial et al., "Rotational Frequency Shift of a Light Beam," *Phys. Rev. Lett.*, 1998; 81(22):4828–4830.

DUV Spectroscopic Ellipsometry (SE). Therma–Wave Measurement Technologies [retrieved from the Internet on Feb. 11, 2003]. http://www.thermawave.com/technology/duvse.htm. 1 page.

Erman et al., "Spatially resolved ellipsometry", *J. Appl. Phys.*, 1986; 60(3):859–873.

Goodman, Introduction to Fourier Optics, 2d ed., New York, 1996; cover page, title page and table of contents, 8 pgs.

Gu (editor), *Advanced Optical Imaging Theory*, Springer Series in Optical Sciences, New York, 2000, 8 pgs.

Hafizi et al., "Laser–driven acceleration with Bessel beams," *Phys. Rev. E*, 1997; 55(3):3539–3545.

Harada et al., "Radiation forces on a dielectric sphere in the Rayleigh scattering regime," *Optics Comm.*, 1996; 124:529–541.

He et al., "Direct Observation of Transfer of Angular Momentum to Absorptive Particles from a Laser Beam with a Phase Singularity," *Phys. Rev. Lett.*, 1995; 75(5):826–829.

Hsieh et al., "Image contrast in polarization microscopy of magneto–optical disk data–storage media through birefringent plastic substrates," *Appl. Opt.*, 1997; 36(20):4839–4852.

I–Elli2000 Imaging Ellipsometer. Nano–film Technologie [retrieved on Jan. 15, 2001]. Retrieved from Internet: <URL: http:www.nanofilm.ed/html/elli2000/body_i–elli2000.html>, 16 pages.

Imaging Ellipsometer. Beaglehole Instruments [retrieved on Jan. 15, 2001]. Retrieved from Internet: <URL: http://www.beaglehole.com/imelli/im–main.html>, 9 pages.

Jin et al., "Imaging ellipsometry revisited: Developments for visualization of thin transparent layers on silicon substrates", *Rev. Sci. Instrum.* 1996; 67(8):2930–3935.

Kano et al., "Excitation of surface–plasmon polaritons by a focused laser beam," *J. Opt. Soc., Am. B*, 1998; 15(4):1381–1386.

Karlsson, "Detector and Data Acquisition System for an Imaging Ellipsometer", IEEE Instrumentation and Measurement Technology Conference, St. Paul, Minnesota, USA, May 18–21, 1998; I:679–682.

Kuga et al., "Novel Optical Trap of Atoms with a Doughnut Beam," *Phys. Rev. Lett.*, 1997; 78(25):4713–4716.

Leng et al., "Characterization of titanium nitride (TiN) films on various substrates using spectrophotometry, beam profile reflectometry, beam profile ellipsometry and spectroscopic beam profile ellipsometry", *Thin Solid Films*, 1988; 313–314:308–313.

Leng et al., "Combined beam profile reflectrometry, beam ellipsometry and ultraviolet–visible spectrophotometry for the characterization of ultrathin oxide–nitride–oxide films on silicon", *J. Vac. Sci. Tech.*, 1999: A17(2):380–384.

Liu et al., "Image scanning ellipsometry for measuring nonuniform film thickness profiles", *Applied Optics*, 1994; 33(7):1223–1229.

Liu et al., "Vector diffraction from subwavelength optical disk structures: two–dimensional modeling of near–field profiles, far–field intensities, and detector signals from a DVD," *Appl. Opt.*, 1999; 38(17):3787–3797.

Logofatu et al., "Identity of the cross–reflection coefficients for symmetric surface–relief gratings", *J. Opt. Soc. Am. A*, 1999; 16(5):1108–1114.

Mansfield et al., "Solid immersion microscope", *Appl. Phys. Lett.*, 1990; 57(24):2615–2616.

Mansuripur, "Certain computational aspects of vector diffraction problems", *J. Opt. Soc. Am. A*, 1989; 6(5):786–805.

Mansuripur, "Distribution of light at the near the focus of high–numerical–aperture objectives", *J. Opt. Soc. Am. A*, 1986; 3(12):2086–2093.

Mansuripur, *The Physical Principles of Magneto–Optical Recording*, Cambridge, Mass. 1995; cover page, title page, table of contents, 10 pgs.

Minhas et al., "Ellipsometic scatterometry for the metrology of sub–0.1–$\mu$m–linewidth structures," *Appl. Opt.*, 1998; 37(22):5112–5115.

Mirotznik et al., "Three–Dimensional Vector–Based Analysis of Sub–Wavelength Diffractive Optical Elements Using the Finite–Difference Time–Domain (FDTD) Method," *Diffractive Optics and Micro–Optics*, 10; 1998, OSA Technical Digest Series (Optical Society of America, Washington, D.C.); 91–93.

Mirotznik et al., "A hybrid finite element–boundary element method for the analysis of diffractive elements," *J. Mod. Opt.*, 1996; 43(7):1309–1321.

Moharam et al., "Diffraction analysis of dielectric surface–relief gratings," *J. Opt. Soc. Am.*, 1982; 72(10):1385–1392.

Moharam et al., "Formulation for stable and efficient implementation of the rigorous coupled–wave analysis of binary gratings," *J. Opt. Soc. Am. A*, 1995; 12(5):1068–1076.

Moharam et al., "Stable implementation of the rigorous coupled–wave analysis for surface–relief gratings: enhanced transmittance matrix approach," *J. Opt. Soc. Am. A*, 1995; 12(5):1077–1086.

Niziev et al., "Influence of beam polarization on laser cutting efficiency," *J. Phys. D*, 1999; 32:1455–1461.

Nordin et al., "Broadband form birefringent quarter–wave plate for the mid–infrared wavelength region", *Optics Express*, 1999; 5(8):163–168.

Oron et al., "Efficient formation of pure helical laser beams," *Optics Comm.*, 2000; 182:205–208.

Oron et al., "The formation of laser beams with pure azimuthal or radial polarization," *Appl. Phys. Lett.*, 2000; 77(21):3322–3324.

Otaki et al., "Polarization effect on signal from optical ROM using solid immersion lens," *Jpn. J. Appl. Phys.*, 2000; 39:698–706.

Paesler et al, "Optical Tunneling Microscopes," *Near–Field Optics, Theory, Instrumentation, and Applications*, New York, New York, 1996, 143–161.

Prather et al., "Formulation and application of the finite–difference time–domain method for the analysis of axially symmetric diffractive optical elements," *J. Opt. Soc. Am. A*, 1999; 16(5):1131–1142.

Quabis et al., "The focus of light–theoretical calculation and experimental tomographic reconstruction," *Appl. Phys. B*, 2001; 72:109–113.

Raether, *Surface on Smooth and Rough Surfaces and on Gratings*, Springer–Verlag, Berlin, 1988, cover page, title page, table of contents 4 pgs.

Richards et al., "Electromagnetic diffraction in optical systems II. Structure of the image field in an aplanatic system," *Proc. R. Soc. London Ser. A*, 1959; 253:358–379.

Rosencwaig et al., "Beam profile reflectometry: a new technique for dielectric film measurements", *Appl. Phys. Lett.*, 1992; 60(11):1301–1303.

Rothenhäusler et al., "Surface–plasmon microscopy," *Nature*, 1998; 332:615–617.

Sato et al., "Optical trapping of microscopic metal particles," *Opt. Lett.*, 1994; 19(22):1807–1809.

See et al., "Scanning optical microellipsometer for pure surface profiling", *Applied Optics*, 1996; 35(34):6663–6668.

Somekh et al., "Optical V(z) for high resolution $2\pi$ surface plasmon microscopy," *Opt. Lett.*, 2000; 25(11):823–825.

Spesivtsev et al., "Automatic Scanning Microellipsometer", *Optoelectr., Instrum. and Data Process.*, 1997; 1:90–94.

Stalder et al., "Linearly polarized light with axial symmetry generated by liquid–crystal polarization converters," *Opt. Lett.*, 1996; 21(23):1948–1950.

Taflove et al., *Computational Electrodynamics—The Finite–Difference Time–Domain Method*, Boston, Mass., 1995; cover page, title page, table of contents, 13 pgs.

Tominaga et al., "Local Plasmon photonic transistor," *Appl. Phys. Lett.*, 2001; 78(17):2417–2419.

Tompkins, *A User's Guide to Ellipsometry*, Boston, Mass., 1993; cover page, title page, table of contents, 9 pgs.

Tompkins et al., "Spectroscopic Ellipsometry and Reflectometry", N.Y., John Wiley & Sons, Inc.; 1999.

Wang et al. "Measuring and modeling optical diffraction from subwavelength features," *J. Opt. Soc. Am. A*, 2001; 18(3):565–572.

Wolf, "Electromagnetic diffraction in optical systems I. An integral representation of the image field," *Proc. R. Soc. Ser. A*, 1959; 253:349–357.

Wu et al., "Realization of numerical aperture 2.0 using a gallium phosphide solid immersion lens," Applied Physics Letters, 1999; 75(26):4064–4066.

Ye, "Non mechanical half–wave plate polarization rotator", *Optik*, 1995; 101(2):77–79.

Youngworth et al., "Focusing of high numerical aperture cylindrical–vector beams," *Optics Express*, 2000; 7(2):77–87.

Zhan et al., "Focus shaping using cylindrical vector beams," *Optics Express*, 2002, 10(7):324–331.

Zhan et al., Imaging ellipsometry for high–spatial–resolution metrology, University of Minnesota, Minneapolis, MN, SPIE Proceedings, vol. 4435, Wave optics and VLSI photonic devices for information processing, 2001; 65–76.

Zhan et al., "Interferometric measurement of the geometric phase in space–variant polarization manipulations," *Optics Communications*, 2002; 213:241–245.

Zhan et al., "Measurement of surface features beyond the diffraction limit using an imaging ellipsometer," *Optics Letters*, 2002; 27(10):821–823.

"Optical Methods for Thickness Measurements on Thin Metal Films", Pokrovsky, App. Optics, vol. 30, No. 22 (Aug. 1, 1991).*

"Differential Reflection Phase Shift Under Conditions of Attenuated Internal Reflection", Azzame J. Opt. Soc. Am. A, vol. 16, No. 7 (Jul. 1999).*

"Solid Immersion Microscope", Mansfield et al., Appl. Phys Lett. 57(24), (Dec. 10, 1990).*

"Characterization of Fabrication Damage in SrT iO3 By Internal and External Measurements", Bu–Abbud & Bashara, Surface Science 96 (1980).*

* cited by examiner

ELLIPSOMETRY METHODS AND APPARATUS USING SOLID IMMERSION TUNNELING

CROSS REFERENCE TO RELATED APPLICATIONS

This is a Continuation-in-Part of U.S. patent application Ser. No. 09/691,346 filed on 18 Oct. 2000, now U.S. Pat. No. 6,693,711 entitled "Ellipsometer Using Radial Symmetry", and claims the benefit of U.S. Provisional Patent Application No. 60/364,475, filed 15 Mar. 2002, which are hereby incorporated by reference.

BACKGROUND OF THE INVENTION

The present invention relates generally to ellipsometry. More particularly, the present invention pertains to ellipsometric methods and apparatus using solid immersion tunneling.

Ellipsometry is an optical technique that uses polarized light to probe the properties of a sample. The most common application of ellipsometry is the analysis of thin films. Through the analysis of the state of polarization of the light that interacts with the sample, ellipsometry can yield information about such films. For example, depending on what is already known about the sample, the technique can probe a range of properties including the layer thickness, index of refraction, morphology, or chemical composition.

Generally, optical ellipsometry can be defined as the measurement of the state of polarized light waves. An ellipsometer measures the changes in the polarization state of light when it interacts with a sample. The most common ellipsometer configuration is a reflection ellipsometer, although transmission ellipsometers are sometime used. If linearly polarized light of a known orientation is reflected or transmitted at oblique incidence from a sample surface, then the resultant light becomes elliptically polarized. The shape and orientation of the ellipse depends on the angle of incidence, the direction of the polarization of the incident light, the wavelength of the incident light, and the Fresnel properties of the surface. The polarization of the light is measured for use in determining characteristics of the sample. For example, in one conventional null ellipsometer, the polarization of the reflected light can be measured with a quarter-wave plate followed by an analyzer. The orientation of the quarter-wave plate and the analyzer are varied until no light passes though the analyzer, i.e., a null is attained. From these orientations and the direction of polarization of the incident light, a description of the state of polarization of the light reflected from the surface can be calculated and sample properties deduced.

Two characteristics of ellipsometry make its use particularly attractive. First, it is a nondestructive technique, such that it is suitable for in situ observation. Second, the technique is extremely sensitive. For example, it can measure small changes of a film down to sub-monolayer of atoms or molecules. For these reasons, ellipsometry has been used in physics, chemistry, materials science, biology, metallurgical engineering, biomedical engineering, etc.

As mentioned above, one important application of ellipsometry is to study thin films, e.g., in the fabrication of integrated circuits. In the context of ellipsometry, a thin film includes films over a variety of thickness. The sensitivity of an ellipsometer is such that a change in film thickness of a few angstroms can usually be detected. From the measurement of changes in the polarization state of light when it is reflected from a sample, an ellipsometer can measure the refractive index and the thickness of thin films, e.g., semi-transparent thin films. The ellipsometer relies on the fact that the reflection at a material interface changes the polarization of the incident light according to the index of refraction of the interface materials. In addition, the polarization and overall phase of the incident light is changed depending on the refractive index of the film material as well as its thickness.

Generally, for example, a conventional reflection ellipsometer apparatus, such as shown in FIG. 1, includes a polarizer arm 12 and an analyzer arm 14. The polarizer arm 12 includes a light source 15 such as a laser (commonly a 632.8 nm helium/neon laser or a 650–850 nm semiconductor diode laser) and a polarizer 16, which provides a state of polarization for the incident light 18. The polarization of the incident light may vary from linearly polarized light to elliptically polarized light to circularly polarized light. The incident light 18 is reflected off the sample 10 or layer of interest and then analyzed with the analyzer arm 14 of the ellipsometer apparatus. The polarizer arm 12 of the ellipsometer apparatus produces the polarized light 18 and orients the incident light 18 at an angle 13 with respect to a sample plane 11 of the sample 10 to be analyzed, e.g., at some angle such as 20 degrees with respect to the sample plane 11 or 70 degrees with respect to the sample normal.

The reflected light 20 is examined by components of the analyzer arm 14, e.g., components that are also oriented at the same fixed angle with respect to the sample plane 11 of the sample 10. For example, the analyzer arm 14 may include a quarter wave plate 22, an analyzer 24 (e.g., a polarizer generally crossed with the polarizer 16 of the polarizer arm 12), and a detector 26. To measure the polarization of the reflected light 20, the operator may change the angle of one or more of the polarizer 16, analyzer 24, or quarter wave plate 22 until a minimal signal is detected. For example, the minimum signal is detected if the light 20 reflected by the sample 10 is linearly polarized, while the analyzer 24 is set so that only light with a polarization that is perpendicular to the incoming polarization is allowed to pass. The angle of the analyzer 24 is therefore related to the direction of polarization of the reflected light 20 if the minimum condition is satisfied. The instrument is "tuned" to this null (e.g., generally automatically under computer control), and the positions of the polarizer 16, the analyzer 24, and the incident angle 13 of the light relative to the sample plane 11 of the sample 10 are used to calculate the fundamental quantities of ellipsometry: the so called (psi ($\Psi$), delta ($\Delta$)) pair given by:

$$\frac{r_p}{r_s} \tan\Psi(e^{j\Delta})$$

where $r_p$ and $r_s$ are the complex Fresnel reflection coefficients for the transverse magnetic and transverse electrical waves of the polarized light, respectively. For example, from the ellipsometry pair ($\Psi$, $\Delta$), the film thickness and index of refraction can be determined. It will be recognized that various ways of analyzing the reflected light may be possible. For example, one alternative is to vary the angle of the quarter wave plate and analyzer to collect polarization information.

Advances in microelectronics fabrication are rapidly surpassing current capabilities in metrology. In order to enable future generations of microelectronics, advanced specific metrology capabilities must be developed. Key among these metrology capabilities is the ability to measure the properties of ultra-thin films over sub-micron lateral dimensions.

As used herein, ultrathin film refers to a film having a thickness of less than 100 angstroms.

Currently available ellipsometric techniques that measure material properties generally measure them over a large area. In other words, polarization measurements have been traditionally used to determine the thickness and refractive index of homogeneous films over a relatively large area. However, in many cases determining the thickness and refractive index of homogeneous films over a relatively large area is inadequate for exceedingly small-featured structures. Since the polarization state is affected significantly by diffraction from sub-micron features, the shape of such sub-micron features (e.g., critical dimensions of lateral or transverse structures such as gate dielectrics for transistor structures) may be difficult to measure using current ellipsometric techniques that determine thickness and refractive index over relatively large areas. For example, the smallest spot that a conventional ellipsometer can measure is generally determined by the beam size, usually on the order of hundreds of microns. This essentially limits the application of conventional ellipsometers to samples with large and uniform interface characteristics.

Existing ellipsometers have difficulties in measuring characteristics (e.g., index of refraction, thickness, etc.) for ultrathin films. This may be due, at least in part, to the fact that conventional ellipsometry models do not provide adequate accuracy when such ultrathin films are being characterized (e.g., when ellipsometric measurements are being processed). For example, a small error in a $\psi$ measurement from a conventional ellipsometer apparatus can skew determination of the refractive index significantly when such models are used. Thus, conventional ellipsometers may, in many cases, be unsuitable to measure characteristics, such as refractive index, for films that are thinner than 100 angstroms.

SUMMARY OF THE INVENTION

The present invention provides an ellipsometer apparatus and methods that can be used for accurately measuring properties of thin films. In one embodiment, such apparatus and methods are particularly advantageous where the thin film is an ultrathin film having a thickness of less than 100 angstroms.

The present invention exploits the use of a solid immersion apparatus (e.g., a prism or an objective lens in combination with a solid immersion lens) that facilitates optical tunneling, which provides accurate ellipsometric measurements for thin films, particularly for ultrathin films having a thickness of less than 100 angstroms. One or more embodiments of the present invention provide additional capabilities including the use of solid immersion tunneling to measure ultrathin films with improved spatial resolution (e.g., on the order of 100 nanometers). The present invention also includes modeling and model fitting techniques for processing ellipsometric signals to provide enhanced capabilities and improved measurement accuracy. Further, in one or more embodiments, the present invention may provide enhanced accuracy by using a technique during model fitting (e.g., using regression analysis) in which one or more ellipsometric parameters are given more weight than other ellipsometric parameters. The present invention may also provide an ellipsometric technique that can measure some thin film sample characteristics over a wide range of film thickness (e.g., ultrathin films and those films having a greater thickness than ultrathin films).

An ellipsometry method according to the present invention includes receiving one or more ellipsometric signals corresponding to at least one ray of polarized light provided at an angle greater than a critical angle of a solid immersion apparatus. The solid immersion apparatus includes a surface located adjacent a thin film of a sample. The method further includes determining one or more measured ellipsometric parameters as a function of the one or more ellipsometric signals for the at least one ray of the polarized light provided at an angle greater than the critical angle and then determining at least one characteristic (e.g., thickness or index of refraction) of the thin film by fitting the one or more measured ellipsometric parameters to a model. The model provides a relationship between the at least one characteristic for thin films and model ellipsometric parameters corresponding to the one or more measured ellipsometric parameters.

In one embodiment of the method, the model may provide a relationship between the at least one characteristic for thin films having a thickness less than 100 angstroms and model ellipsometric parameters corresponding to the one or more measured ellipsometric parameters.

In another embodiment of the method, the solid immersion apparatus may include a hemispheric lens or a stigmatic lens.

In another embodiment, the one or more measured ellipsometric parameters may include $\psi$ and $\Delta$ for the at least one ray of the polarized light provided at an angle greater than the critical angle.

In yet another embodiment of the method, the method includes receiving one or more ellipsometric signals corresponding to at least one ray of polarized light provided at an angle less than the critical angle of the solid immersion apparatus and determining one or more ellipsometric parameters as a function of the one or more ellipsometric signals for the at least one ray of the polarized light provided at an angle less than the critical angle. The at least one characteristic is then determined based on one or more measured ellipsometric parameters determined for the at least one ray of the polarized light provided at an angle less than the critical angle and one or more measured ellipsometric parameters determined for the at least one ray of the polarized light provided at an angle less than the critical angle.

In various embodiments, the solid immersion apparatus may include a prism or, for example, an objective lens and a solid immersion lens (e.g., a solid immersion lens adjacent the thin film but separated therefrom by a substrate upon which the thin film is provided, a solid immersion lens having a surface separated from the sample by a distance, or a surface of the solid immersion lens being positioned in contact with the sample).

An ellipsometer apparatus according to the present invention includes an interface apparatus operable to receive one or more ellipsometric signals corresponding to at least one ray of polarized light provided at an angle greater than a critical angle of a solid immersion apparatus. The solid immersion apparatus includes a surface adapted to be positioned adjacent a thin film of a sample. The apparatus further includes a processing apparatus operable to determine one or more measured ellipsometric parameters as a function of the one or more ellipsometric signals for the at least one ray of the polarized light provided at an angle greater than the critical angle and determine at least one characteristic of the thin film by fitting the one or more measured ellipsometric parameters to a model. The model provides a relationship between the at least one characteristic for thin films and model ellipsometric parameters corresponding to the one or more measured ellipsometric parameters.

Various embodiments may include one or more features for carrying out one or more methods or processes described herein. For example, the apparatus may include a model that provides a relationship between the at least one characteristic for thin films having a thickness less than 100 angstroms and model ellipsometric parameters corresponding to the one or more measured ellipsometric parameters; a prism that includes a surface adapted to be located adjacent the thin film of the sample; a hemispheric lens or a stigmatic lens; a surface of a solid immersion apparatus that is positioned in contact with the sample or one that is separated from the sample by a distance; etc.

The above summary of the present invention is not intended to describe each embodiment or every implementation of the present invention. Advantages, together with a more complete understanding of the invention, will become apparent and appreciated by referring to the following detailed description and claims taken in conjunction with the accompanying drawings.

DETAILED DESCRIPTION OF THE EMBODIMENTS

Solid immersion tunneling ellipsometer methods and apparatus shall be described herein with reference to FIGS. 2–13. In the following detailed description of the embodiments, reference is made to the drawings that form a part thereof, and in which are shown by way of illustration specific embodiments in which the invention may be practiced. It is to be understood that other embodiments may be utilized, as structural or process changes may be made without departing from the scope of the present invention.

Figure 1:
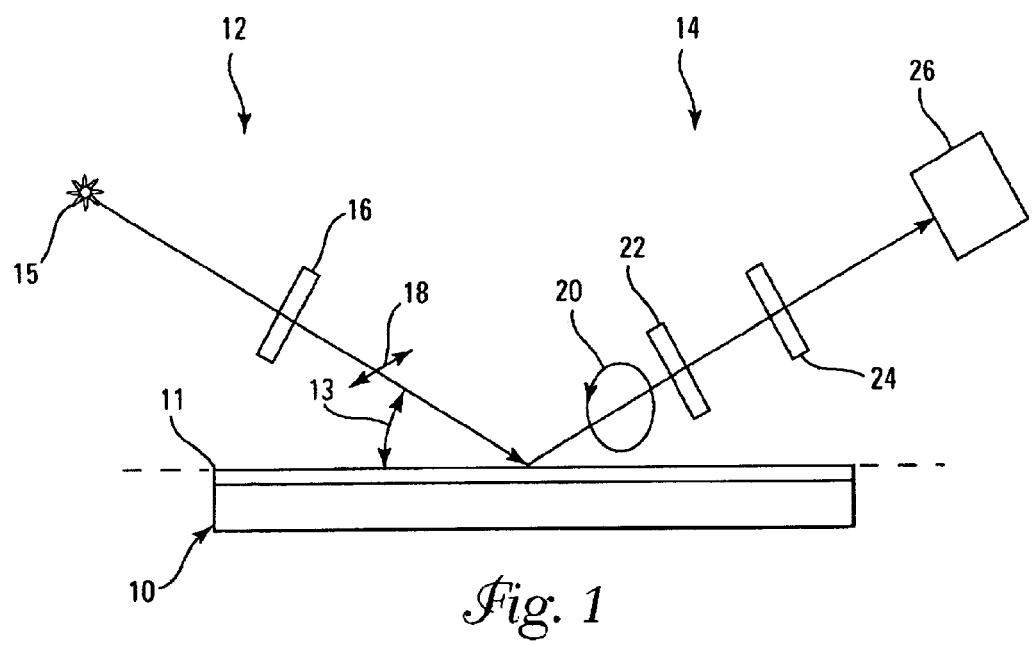
FIG. 1 is a diagram of a conventional ellipsometer.
Figure 2:
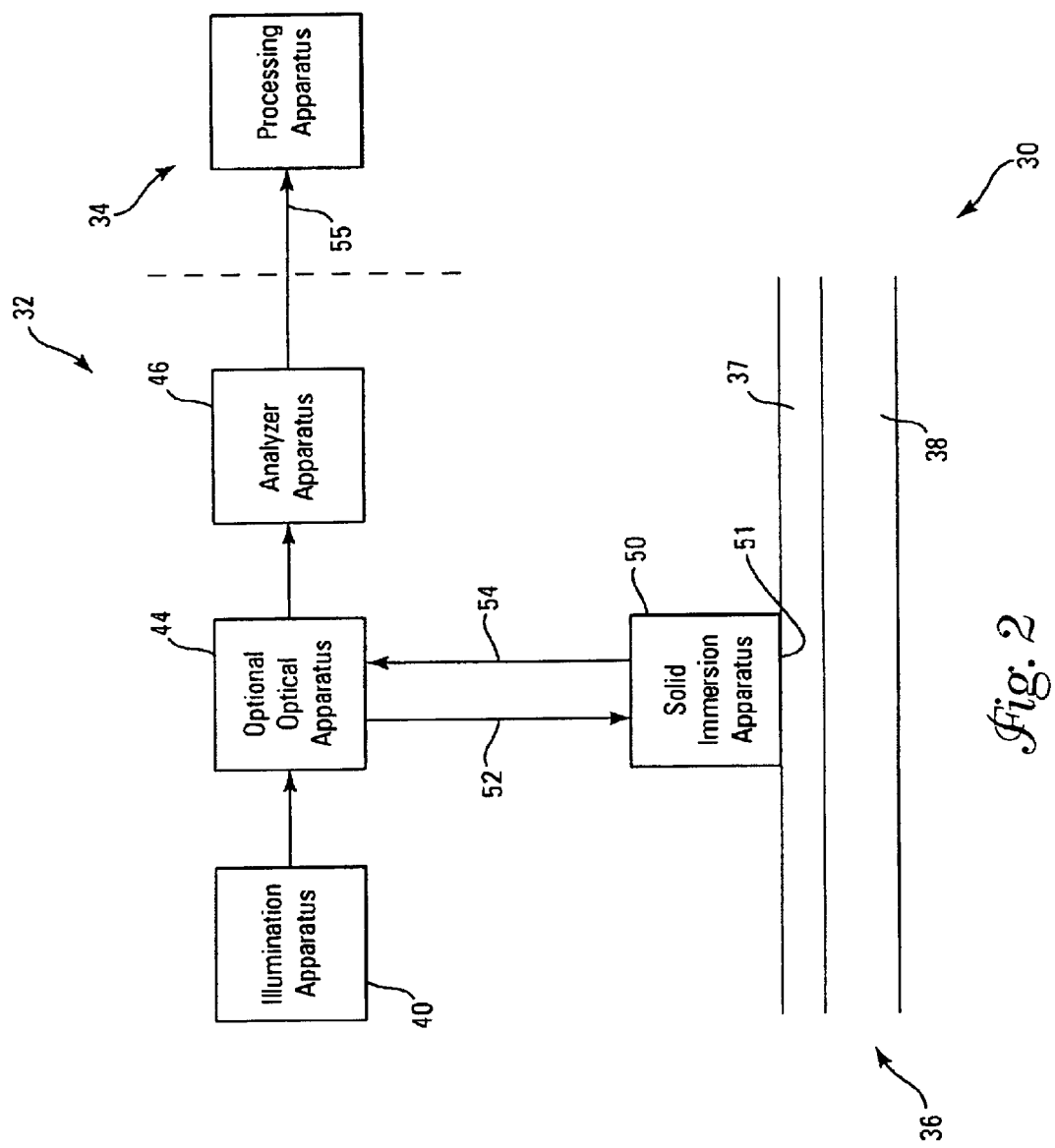
FIG. 2 is one illustrative general diagram of a solid immersion tunneling ellipsometer system according to the present invention.

FIG. 2 shows a general illustration of a solid immersion tunneling ellipsometer system 30 operable for carrying out one or more ellipsometry methods according to the present invention with respect to a sample 36. The sample 36 includes a thin film 37 to be characterized provided on a substrate 38.

The solid immersion tunneling ellipsometer system 30 is operable to determine one or more characteristics of various thin films and/or structures. Examples of characteristics that may be measured include: thickness and index of refraction of a single film; thickness and indexes of refraction of multiple films; index of refraction of a substrate; absorption of a thin film; absorptions of multiple films; stress of thin films; surface roughness; material composition; and magnetic properties.

One skilled in the art will recognize that the present invention may be used to characterize different types of films provided on a substrate. Furthermore, the present invention may be used to characterize one or more thin films on a substrate or a thin film that may include one or more layers. Examples of the types of films that may be characterized are biological samples, metallic films, and dielectric films.

In one embodiment, the sample 36 may include a thin film formed on the substrate 38. In another embodiment, the sample 36 may include an ultrathin film formed on the substrate 38. Yet in another embodiment, the sample may include a dielectric thin film provided on the substrate 38. Yet in another embodiment, the sample may include a high dielectric constant thin film provided on the substrate 38. Yet further, in another embodiment, the sample 36 may include a gate oxide (e.g., silicon oxide, silicon oxynitride, silicon nitride, etc.) formed on a substrate (e.g., silicon substrate.

The solid immersion tunneling ellipsometer system 30 includes an ellipsometer apparatus 32 and a processing apparatus 34 (e.g., a computer executing suitable software). The ellipsometer apparatus 32 performs physical measurements on the sample 36, and the results, in the form of ellipsometric signals 55, are provided to the processing apparatus 34 for processing. In this application, ellipsometric signals are defined as any signals or information that is provided by the ellipsometer apparatus 32 to the processing apparatus 34 for use in determining one or more characteristics of the sample. For example, an illumination apparatus 40 of the ellipsometer apparatus 32 may provide information including the wavelength and polarization of the incident light, and the angle of incidence. As a further example, an analyzer apparatus 46 of the ellipsometer apparatus 32 may provide information including the intensity of the reflected light in a specific state of polarization, and the nulling positions and angles related to the reflected light. The processing apparatus 34 uses the ellipsometric signals 55 to determine one or more ellipsometric parameters (e.g., ψ and Δ) which are then used to determine one or more characteristics of the film 37 (e.g., index of refraction, thickness, etc.).

As shown generally in FIG. 2, the ellipsometer apparatus 32 includes the illumination apparatus 40, an optional optical apparatus 44, the analyzer apparatus 46, and a solid immersion apparatus 50 (e.g., a prism or an objective lens in combination with a solid immersion lens). Such a general configuration will be apparent to one skilled in the art when viewed with reference to more detailed embodiments shown in FIGS. 2, 6, and 7.

Generally, polarized light 52 is provided to the solid immersion apparatus 50 from the illumination apparatus 40. With the solid immersion apparatus 50 having a surface 51 located adjacent the film 37, tunneling occurs for incident light provided at an angle greater than a critical angle of the solid immersion apparatus 50. Elliptically polarized light 54 is provided as the reflected light from the film 37. The elliptically polarized light 54 is provided to the analyzer apparatus 46. Upon operation of the analyzer apparatus 46, ellipsometric signals 55 representative of the reflected light are provided to the processing apparatus 34. The optional optical apparatus 44, for example, may be a beam splitter configuration such as described with reference to FIG. 7 or may not be required such as with use of a prism in the ellipsometer apparatus configuration of FIG. 4.

Generally, the method of determining the one or more characteristics of the thin film 37 of sample 36 is based on associating the measured ellipsometric parameters (e.g., determined using measurements from ellipsometer apparatus 32) with a mathematical model based on the same ellipsometric parameters generated using a model of an event. An event, as used herein, refers to a physical measurement performed using the ellipsometer apparatus 32 (e.g., incident light at greater than the critical angle and the measurement of the reflected light with the result of the event being measured ellipsometric signals; incident light at less than the critical angle and the measurement of the reflected light with the result of the event being measured ellipsometric signals, etc.).

A model, as used herein, refers to a mathematical description of an event, and trajectories that are generated from the mathematical description. Trajectories, as used herein, refer to information (e.g., a set of graphs, a lookup table, etc.) generated using the mathematical description which provide the relationship between one or more ellipsometric parameters (e.g., ψ, Δ) and one or more characteristics (e.g., thickness) of the thin films to be characterized. Thus, the processing apparatus 34 uses the measured ellipsometric parameters, along with modeled ellipsometric parameters (e.g., a set of trajectories or some other relational information), to determine at least one characteristic of the sample 36 (e.g., index of refraction of the film 37, thickness of the film 37, etc.).

Figure 3A:
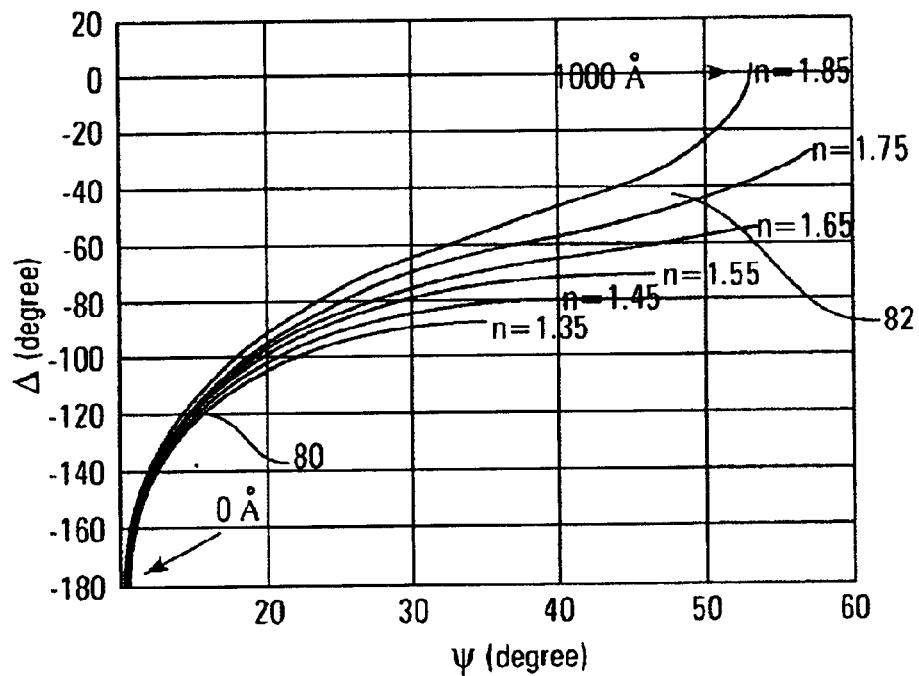
FIG. 3A and FIG. 3B illustrate an example trajectory diagram associated with a conventional ellipsometer and an example trajectory diagram associated with a solid immersion tunneling ellipsometer system such as shown generally in FIG. 2.
Figure 3B:
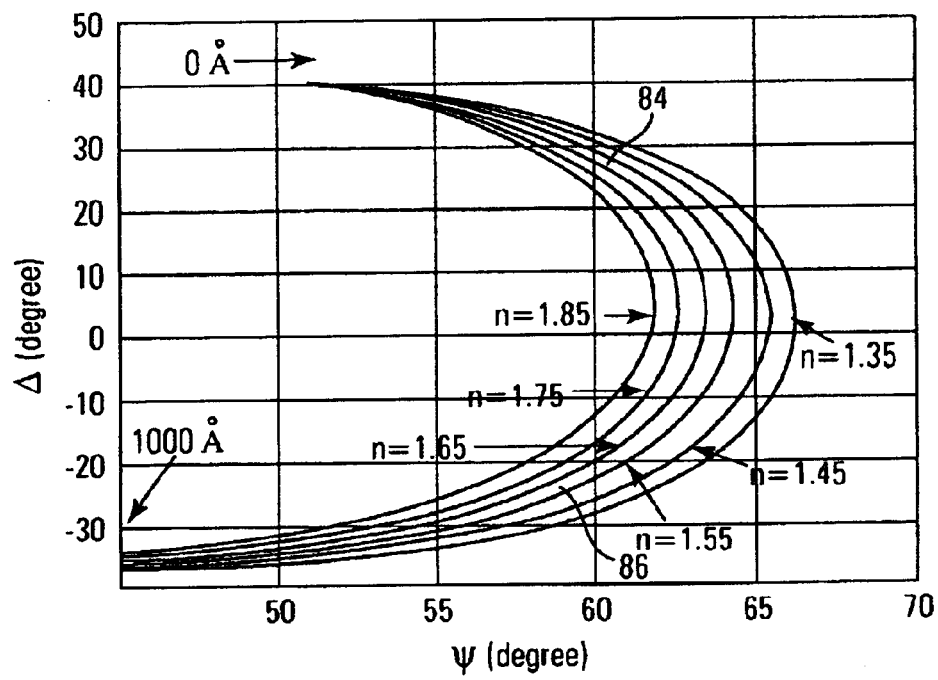

Conventional ellipsometers, in many instances, have difficulties in measuring characteristics such as the index of refraction of ultrathin films. This is due, at least in part, to the fact that (ψ, Δ) trajectories used for determining the index of refraction are not well separated in the ultrathin regime, as illustrated in FIG. 3A. FIGS. 3A and 3B show examples of trajectories in a graphic format that can be used to express the relationship between the one or more sample characteristics (e.g., thickness and index of refraction) and the ellipsomatic parameters (e.g., ψ and Δ). The x-axis corresponds to the ψ value and y-axis corresponds to the Δ value, thus any value of a ψ, Δ pair indicates a point on the graph. Note that each curve on the graph corresponds to a particular value of the index of refraction, and that along each curve, the individual dots indicate the thickness of the sample, where each dot along the curve represents a thickness change of 10 angstroms. Note the difference between FIG. 3A and FIG. 3B. In FIG. 3A, the thinnest films are at the bottom left, and the thickness increases as the curve goes to the upper right; for FIG. 3B, the thinnest films are at the upper left, and the thickness increases as the curve goes to the lower left. To determine a sample characteristic, the measured ψ, Δ pair is used to select a point on the graph, from which the sample characteristics can be determined by selecting the closest curve (which determines the index of refraction) and then on that curve, finding the closest dot (which determines the thickness). Note that fitting can be performed in the case of a ψ, Δ pair that is between curves and/or between dots. Note that for this example, the ellipsometric system is able to determine both the index of refraction and thickness simultaneously.

As shown in FIG. 3A, in region 80 (i.e., the region corresponding to film thickness less than or equal to 100 angstroms), the separation between curves representing different indexes of refraction is minimal, making it difficult to make an accurate measurement. In region 82, corresponding to film thickness of 800 angstroms to 1000 angstroms, the separation is clearer, and more accurate measurements can be made. Thus, when using a conventional ellipsometer to measure ultrathin films, a small error in the ψ value, due to measurement error, can skew the results (e.g., a thickness measurement) significantly. Therefore, conventional ellipsometers are, in many cases, unsuitable to measure the refractive index of ultrathin films. As previously indicated, ultrathin films are films having a thickness of less than 100 angstroms.

The present invention includes a solid immersion tunneling ellipsometric technique that is capable of overcoming the problems of conventional ellipsometric systems such that characteristics of ultrathin films (e.g., thickness and refractive index) can be measured effectively. Such characteristics, like refractive index and thickness, may be determined simultaneously. Moreover, a near-field ellipsometric method using a solid immersion tunneling technique provides accurate thickness and index of refraction measurements with very high spatial resolution. High quality images of the ultrathin films can therefore be obtained through scanning (e.g., as opposed to providing such characteristics for a small spot). Any suitable scanning apparatus may be used to provide measurements over a larger area for providing an image.

To accurately measure, for example, a refractive index, it is advantageous to separate the (ψ, Δ) trajectories along the ψ direction. In other words, one wants to choose an event type that corresponds to trajectories in which the (ψ, Δ) trajectories along the ψ direction provide good separation. To achieve this, a technique and apparatus was developed that utilizes optical tunneling. Such optical tunneling provides a desired ψ-resolution enhancement that will be apparent from the description herein, particularly the description with reference to the following FIG. 4.

Figure 4:
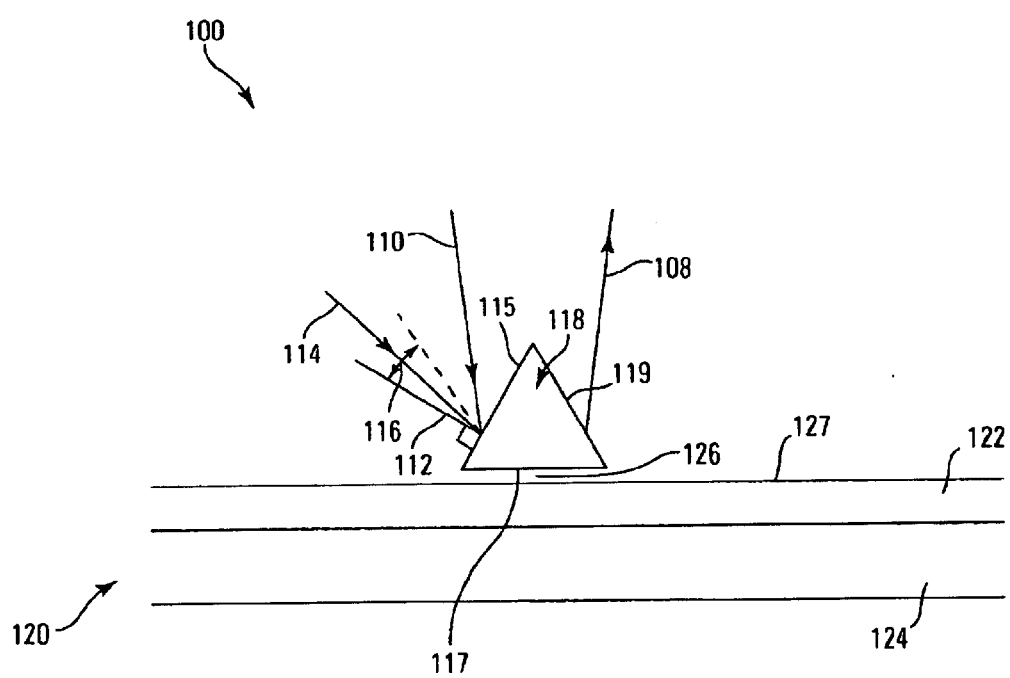
FIG. 4 shows one illustrative diagram of an embodiment of the solid immersion tunneling ellipsometer system shown generally in FIG. 2, using a solid immersion prism, according to the present invention.

FIG. 4 shows an illustrative diagram of one embodiment of a portion of the ellipsometer system shown generally in FIG. 2. The solid immersion tunneling ellipsometer apparatus 100 shown in FIG. 4 utilizes a solid immersion prism 118. The ellipsometer apparatus 100 is operable to provide ellipsometric signals that may be processed according to the present invention to determine at least one characteristic of thin film 122 provided on substrate 124 of sample 120.

In comparison to the ellipsometry apparatus generally shown in FIG. 2, the solid immersion apparatus 50 includes the prism 118, and the optional optical apparatus 44 is not present. The prism 118 includes an incident surface 115 through which incident light 110 may be received, and a reflection surface 119 through which reflected light 108 may be provided to an analyzer apparatus (not shown). Further, the prism includes a tunneling surface 117 positioned adjacent an upper surface 127 of film 122.

In one embodiment, the sample 120 (e.g., substrate assembly) is in contact with tunneling surface 117 of the prism 118. In another embodiment, the thin film 122 may be separated from the tunneling surface 117 by a narrow gap 126 (e.g., air gap).

In one embodiment, the incident polarized light 110 illuminates the thin film 122 through a high refractive index prism 118. For example, a high refractive index material such as GaP (n=3.4) may be used. However, one skilled in the art will recognize that any prism providing a suitable tunneling surface 117 and a critical angle 116 (as shown relative to normal 112) may be used according to the present invention.

One will recognize that incident light 110 as shown in FIG. 4 is provided at an angle greater than the critical angle 116 of the prism 118. However, incident light may also be provided at less than the critical angle 116 as shown by incident light 114.

With the polarized light 110 incident on the prism 118 at an angle greater than the critical angle 116, an evanescent wave is generated at the prism tunneling surface 117. The evanescent wave can be coupled into a propagating wave, thus causing a decrease in reflectivity from the film 122 back into the prism 118. Such tunneling provides the desired ψ-resolution enhancements mentioned above and further described herein, particularly with reference to FIG. 3B below.

FIG. 3B shows illustrative model ellipsometric parameter (ψ, Δ) trajectories for a tunneling ellipsometer using a solid immersion configuration with an exemplary 10 angstrom air gap. The trajectories in Region 84, which corresponds to ultrathin films, clearly show the ψ-resolution enhancement between different refractive indexes. Another characteristic of this near field technique is that, for films thicker than approximately 100 angstroms, the separation of the trajectories gets smaller as the films get thicker, as shown in region 86. This indicates that solid immersion tunneling ellipsometry is more suitable for ultrathin films and is less suitable for thicker films.

In view of the above, it is recognized that more accurate characteristics may be determined for ultrathin films using the near field solid immersion tunneling aspects of the present invention with measurements taken for incident light greater than the critical angle of the solid immersion configuration (e.g., critical angle of prism 118 or as described further herein the critical angle of a solid immersion lens). Likewise, it is also recognized that more accurate characteristics may be determined for films thicker than ultrathin films using techniques similar to conventional ellipsometry with measurements taken for incident light less than the critical angle of the solid immersion apparatus.

By combining techniques similar to conventional ellipsometry (e.g., using light incident at less than the critical angle of a solid immersion apparatus) with the solid immersion tunneling technique, where incident light at greater than the critical angle is used, an ellipsometry system can provide highly accurate results across a wide range of thin film thickness values. In other words, with further reference to the ellipsometry configuration of FIG. 4, for the incident ray 114 at an angle less than the critical angle, the evanescent fields disappear and the measurement is more similar to a conventional ellipsometer. On the other hand, for the incident ray 110 at an angle greater than the critical angle, a near-field measurement is obtained. Thus, a variable angle solid immersion ellipsometer will be able to accurately measure sample characteristics (e.g., thickness and refractive index) for films with varied thickness as further described herein.

At least in one embodiment, the sample characteristic can be determined by performing a fit of measured ellipsometric parameters (e.g., determined from one or more ellipsometric signals of an ellipsometry apparatus) to a model trajectory or relational information generated from a model of an event (e.g., the model trajectory providing the relationship between one or more sample characteristics and ellipsometric parameters, such as for ultrathin films, based on incident light provided at greater than the critical angle of a solid immersions apparatus of a solid immersion tunneling ellipsometer apparatus).

In one embodiment, a regression algorithm can be used to perform this fitting. The regression process can be any standard regression algorithm. When performing the regression, a merit function can be defined. With some experimental measurements available, for example, (ψ, Δ) pairs, one can use the regression process to find out the best guess for the actual parameters of the sample, such as thickness, index of refraction etc. Normally, the regression algorithm takes a guess of these parameters at the beginning, then uses these parameters and a certain optical model (e.g., an event model as described herein) to calculate the corresponding output parameters (ψ, Δ) pairs. Then it compares the output parameters with the experimental using the merit function and sees how close they are. If it is not close enough, the next estimation of the sample parameters is calculated, and the above process is repeated until a satisfactory estimation of the sample parameters is obtained. The output of the regression process is used as the best estimation of the actual sample parameters.

In some embodiments, the solid immersion apparatus is placed adjacent to the sample surface, and there is a gap between the adjacent surface of the solid immersion apparatus and the surface of the sample thin film. The size of the gap may be included as a model parameter or model fitting parameter. For example, in one embodiment, the gap may be measured using interferometry techniques and the measurement provided for use as a parameter of the model. In another embodiment, the present invention can be used to determine the size of the gap with the gap size being an unknown model fitting parameter. When used as a model fitting parameter, priori knowledge of the spacing is not necessary. In other words, the gap can be considered in the modeling process by either performing the gap measurement and providing the value to the model fitting process or treating the size of the gap as an unknown and determining the size during the model fitting process.

An example of a merit function, Merit Function 1, applicable for use with the present invention is:

$$M = \sum_{i=1}^{N} \left[ \left( \frac{\Delta_i - \Delta(\vec{x})}{\sigma_\Delta} \right)^2 + \left( \frac{\Psi_i - \Psi(\vec{x})}{\sigma_\Psi} \right)^2 \right]$$

where $(\psi_i, \Delta_i)$ are the measured data corresponding to the $i^{th}$ incident angle, $\vec{x}$ is a vector inclusive of the model parameters, $\sigma_\Delta$ and $\sigma_\psi$ are the standard deviations of the (ψ, Δ) measurement, and $\Delta(\vec{x})$ and $\psi(\vec{x})$ are the calculated data points using the optical model and the model parameters. During regression, this merit function is minimized to find the optimum results. This merit function has been used to compare conventional ellipsometry with the solid immersion tunneling ellipsometry of the present invention. One example computer simulation based on this merit function showed a refractive index resolution of +/−0.01 for the solid immersion tunneling ellipsometry of the present invention, as compared to +/−0.15 for conventional ellipsometry. This merit function is applicable to any scenario in which there are multiple measurements.

Even though solid immersion tunneling ellipsometry provides enhanced results compared to conventional ellipsometry for films less than 100 angstroms, its resolution of refraction index degrades for films thinner than 20 angstroms. The ($\psi$, $\Delta$) trajectories of ultrathin films illustrate a complementary behavior between solid immersion tunneling ellipsometry and conventional ellipsometry.

While the $\psi$ resolution is worse for conventional ellipsometry than for tunneling ellipsometry, the $\Delta$ resolution is usually better due to the multiple reflections, which are absent in the tunneling case. Thus, an improved merit function, which contains only $\Delta$ values from measurements less than the critical angle and $\psi$ values from measurements greater than the critical angle, is more immune to noise (e.g., provides more accurate measurements of sample characteristics). This improved merit function, Merit Function 2, which may be used according to the present invention is:

$$M = \sum_j \left( \frac{\Delta_i - \overrightarrow{\Delta(x)}}{\sigma_\Delta} \right)^2 + \sum_j \left( \frac{\Psi_i - \overrightarrow{\Psi(x)}}{\sigma_\Psi} \right)^2$$

where j denotes incident angles that are less than the critical angle and i denotes incident angles greater than the critical angle. Merit Function 2 is only applicable in the scenario where there are multiple measurements, where at least one measurement corresponds to incident light greater than the critical angle of the solid immersion apparatus, and at least one measurement corresponds to incident light at less than the critical angle of the solid immersion apparatus. Merit Function 2 can be considered a subset of Merit Function 1. If in Merit Function 1, $\sigma_\Delta$ goes to infinity (because the $\Delta$ error gets very large for measurements at angles greater than the critical angle) then this term goes to zero. Similarly, if in Merit Function 1, $\sigma_\psi$ goes to infinity (because the $\psi$ error gets very large for measurements at angles less than the critical angle) then this term goes to zero. Example simulations using this merit function have shown regression results for determining the index of refraction for films as thin as 10 angstroms with a resolution of +/−0.003.

The regression analysis can provide an optimization process for a variety of measurement scenarios. For example, where there are multiple measurements and multiple models (e.g., models for greater than and less than the critical angle), an optimization step may be performed to determine the desired sample characteristics by minimizing the total error across all the measurements (which can be based on different models). In addition, during the optimization, a weighting of the ellipsometric parameters can be done to improve the accuracy of results. For example, the weight of parameters that contain significant noise may be reduced.

The solid immersion ellipsometry technique shown in FIG. 4 can be applied to measure a homogeneous film. Its spatial resolution is determined by the incident beam size, which is usually on the order of hundreds of micrometers. For thin films with patterns, it is desirable to be able to characterize the sample with high spatial resolution.

Figure 5:
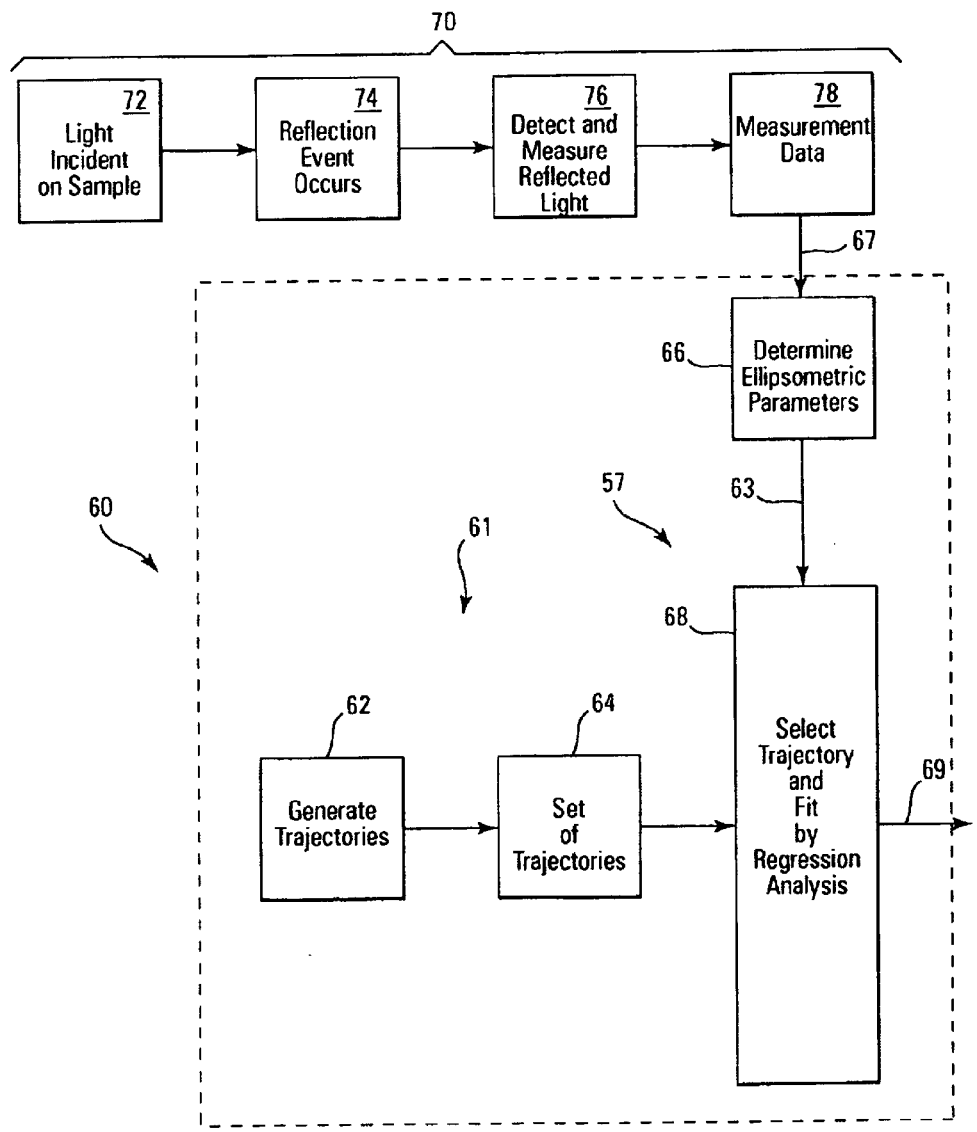
FIG. 5 is a processing flow diagram illustrating one embodiment of a general flow of processing performed in a system such as shown generally in FIG. 2.

FIG. 5 is a processing flow diagram generally illustrating the operation of the system 30 shown generally in FIG. 2. FIG. 5 includes a data processing flow 60 along with a physical measurement flow 70. Physical measurement flow 70 provides a general illustration of the operation of the ellipsometer apparatus 32. One embodiment of the sequence of events of the ellipsometer apparatus 32 includes light 52 incident on the sample 36 at a specified angle (block 72). The incident light reflects off the sample as elliptically polarized light (block 74). The light is measured and detected (block 76) resulting in a set of measurement data 78. The measurement data is provided to the data processing flow 60 in the form of ellipsometric signals 67.

As shown in FIG. 5, the data processing flow 60 generally includes, at least in one embodiment, two components: a modeling component 61 that includes the generation of trajectories 62 and the set of trajectories 64; and a sample characteristic determination component 57 that computes the sample characteristic(s) from the measurement data 78. Sample characteristic determination 57 includes ellipsometric parameter determination 66 and model fitting block 68.

The generate trajectories block 62 includes defining one or more mathematical equations describing the model trajectories for ellipsometric parameters corresponding to those determined or measured using block 66 (e.g., $\psi$, $\Delta$, etc.). Processing one or more equations produces the various model trajectories resulting in the set of model trajectories (block 64). These model trajectories are utilized during the process of determining one or more sample characteristic(s) for the sample 36.

The determine ellipsometric parameters block 66 receives the ellipsometric signals 67 and uses the information to determine ellipsometric parameters 63 representative of the reflected light 54. The ellipsometric parameters 63 and set of model trajectories 64 are used to determine the desired sample characteristics (e.g., thickness). In one embodiment, the measured ellipsometric parameters 63 are fit to a selected model trajectory by regression analysis to provide a resulting desired sample characteristic 69.

The data processing flow 60 may include for example, processing such as generate trajectories 62, determine ellipsometric parameters 66, and model fit by regression analysis 68. One or more of the processing functions performed within data processing flow 60 may be provided using one or more media types.

In one embodiment of the processing flow 60 for a solid immersion tunneling ellipsometer method and apparatus, the ellipsometric signals 67 are determined from at least one reflected ray corresponding to an incident ray at greater than the critical angle. The reflection from the incident ray at greater than the critical angle is influenced by optical tunneling, and is processed using a set of trajectories 64 generated as part of a tunneling model; the tunneling model providing a relationship between the sample characteristic to be determined and one or more model ellipsometric parameters for, preferably, ultrathin films having a thickness less than 100 angstroms.

In another embodiment of the processing flow 60 for a solid immersion tunneling ellipsometer method and apparatus, the ellipsometric signals 67 are determined from at least one reflected ray corresponding to an incident ray at less than the critical angle and greater than the critical angle. The reflection from the incident ray at greater than the critical angle is influenced by optical tunneling, and the reflection from the incident ray at less than the critical angle which is not influenced by optical tunneling, is processed using one or more sets of trajectories 64 generated as part of one or more models.

Figure 6:
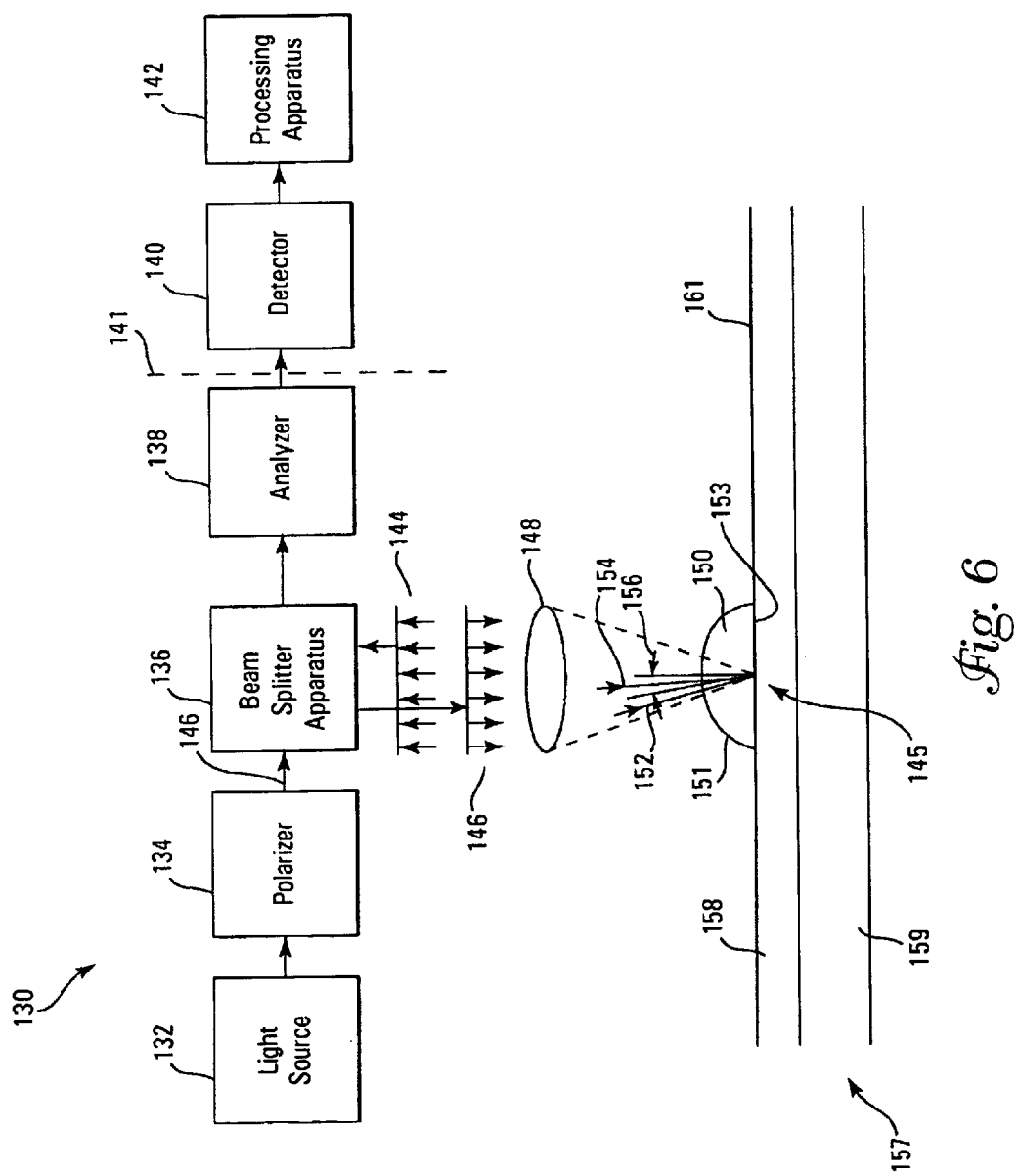
FIG. 6 shows one illustrative diagram of an embodiment of the solid immersion tunneling ellipsometer system shown generally in FIG. 2, using an objective lens focusing polarized light on a solid immersion lens, according to the present invention.

FIG. 6 shows one illustrative diagram of an embodiment of the solid immersion tunneling ellipsometer system 30 shown generally in FIG. 2, using polarized light and a solid immersion lens, according to the present invention. With reference to FIG. 2, the optional optical apparatus 44 is a beam splitter 136 in the FIG. 6 configuration and the solid immersion apparatus 50 is a microscope objective lens 148 and a solid immersion lens 150 in the FIG. 6 configuration.

Solid immersion tunneling ellipsometer system 130 shown in FIG. 6 is used to characterize the thin film 158 provided on substrate 159 of sample 157. The ellipsometer system 130 includes a light source 132 and polarizer 134 used to create incident polarized light 146. However, one of skill in the art will recognize that any manner of providing the polarized light may be used.

The beam splitter directs the polarized light 146 onto the objective lens 148 which focuses the light onto the SIL 150 resulting in a focused spot 145 (e.g., on the bottom tunneling surface 153 of the SIL 150). The hemispherical SIL 150 is placed at the focal plane of the objective lens 148. The existence of the SIL 150 provides higher spatial resolution and optical tunneling for ellipsometric measurement. A spherical surface 151 of the SIL 150 matches the wave front of the focused incident beam. The incident beam is focused to a very small spot at the bottom tunneling surface 153 of the SIL 150 and reflected back from the SIL/sample interface. Optical tunneling will occur for those rays that have incident angles greater than the critical angle 156.

One or more various types of SILs may be used according to the present invention. For example, SILs that are suitable for the present application are the standard SIL (hemispherical lens) and the super SIL (stigmatic lens). These two types of SILs produce non-aberrated spots at the focus point. The SIL shown in FIG. 6 has a hemispherical surface 151 and a planar tunneling surface 153. However, for example, one or more different SILs and super SILs are described in the following references: M. Born and E. Wolf, *Principles of Optics*, 4*th* Edition, Pergamon Press, Oxford, 1970; Ichimura, et al., "High-density optical recording using a solid immersion lens," Applied Optics, v.36 n. 19, pp 4339–4348 (Jul. 1, 1997); Qian et al., "Imaging with solid immersion lenses, spatial resolution, and applications," Proceedings of the IEEE, Vol 88, Issue: 9, pp. 1491–1498 (September 2000); and T. D. Milster, "Near-field optics: a new tool for data storage," Proceedings of the IEEE, Vol. 88, Issue: 9, pp. 1480–1490 (September 2000).

Further, for example, because the incident light 146 is focused to a very small spot 145, the size of the tunneling surface need not be very large. In fact, such a surface may take the form of a probe or more pointed tip. All that is necessary is that the surface be able to couple the evanescent wave to the film to be characterized.

Yet further, the substrate may be used to form a part of the SIL such that the measurements being made for a film on the substrate can be made with the SIL positioned in contact with the back side of the substrate. In this manner, with the SIL and substrate being generally of the same material or at least having similar index of refraction, the substrate actually becomes a part of the SIL 150 and tunneling occurs at the interface between the substrate surface and the thin film to be characterized. In other words, the surface of the solid immersion lens is adjacent the thin film but separated therefrom by a substrate upon which the thin film is provided. In this configuration, the solid immersion lens may include an abbreviated hemispheric lens, wherein the term abbreviated hemispheric lens refers to a lens that has a height less than a hemisphere (i.e., a hemisphere being half of a sphere). As a consequence, in this embodiment, the polarized light is incident on the thin film through the substrate.

It is well known that the field at the back focal plane and the field at the front focal plane are related through a Fourier transform. Thus, each point at the back focal plane corresponds to one ray with a specific incident angle from the front focal plane. By measuring the state of polarization at the back focal plane, ellipsometric signals representative of the SIL/sample interface associated with different incident angles can be provided. The use of the objective lens 148 and SIL 150 creates light incident on the sample at both greater than and less than the critical angle simultaneously, and therefore is capable of providing ellipsometric signals that contain information from both types of angles with a single measurement.

The light reflected from the thin film 158 is directed by the SIL 150 to the objective lens 148. The reflected elliptically polarized light 144 is directed into the beam splitter apparatus 136 and directed to the analyzer 138. The analyzer 138 determines the polarization properties of the reflected light 144. For example, the analyzer 138 may include waveplates, polarizers, polarization rotators, modulators, or any other number of elements as described in R. M. A Azzam and N. M. Bashara, Ellipsometry and polarized light, North Holland Publishing Company, New York (1977).

The light is then received by the detector 140, which measures the intensity of the light and creates a signal proportional to the light intensity. The detector may be a CCD array, a ring CCD, or any other type of light detector that is capable of separating reflected light based on incident light provided greater than the critical angle from reflected light based on incident light provided less than the critical angle. For example, in one embodiment, a ring CCD may be able to provide detection of light returned based on light incident at greater than the critical angle. Further, a CCD array may perform detection of all of the light reflected and then processing may perform a selection of measurements made for reflected light corresponding to the incident light provided at greater than the critical angle. Further, for example, as shown optionally in FIG. 6, a spatial filter 141 may be used to provide reflected light based on the incident light greater than the critical angle (e.g., a spatial filter that allows only an annular ring of reflected light to pass). The above detection would also apply to providing detection of reflected light corresponding to incident light at less than the critical angle.

The analyzer 138 and detector 140 provide information as described herein (e.g., such as intensity of the reflected light in a specific state of polarization, or the nulling positions and angles related to the reflected light.) in the form of ellipsometric signals that are then sent to the processing apparatus 142 to determine at least one characteristic of the sample.

Figure 7:
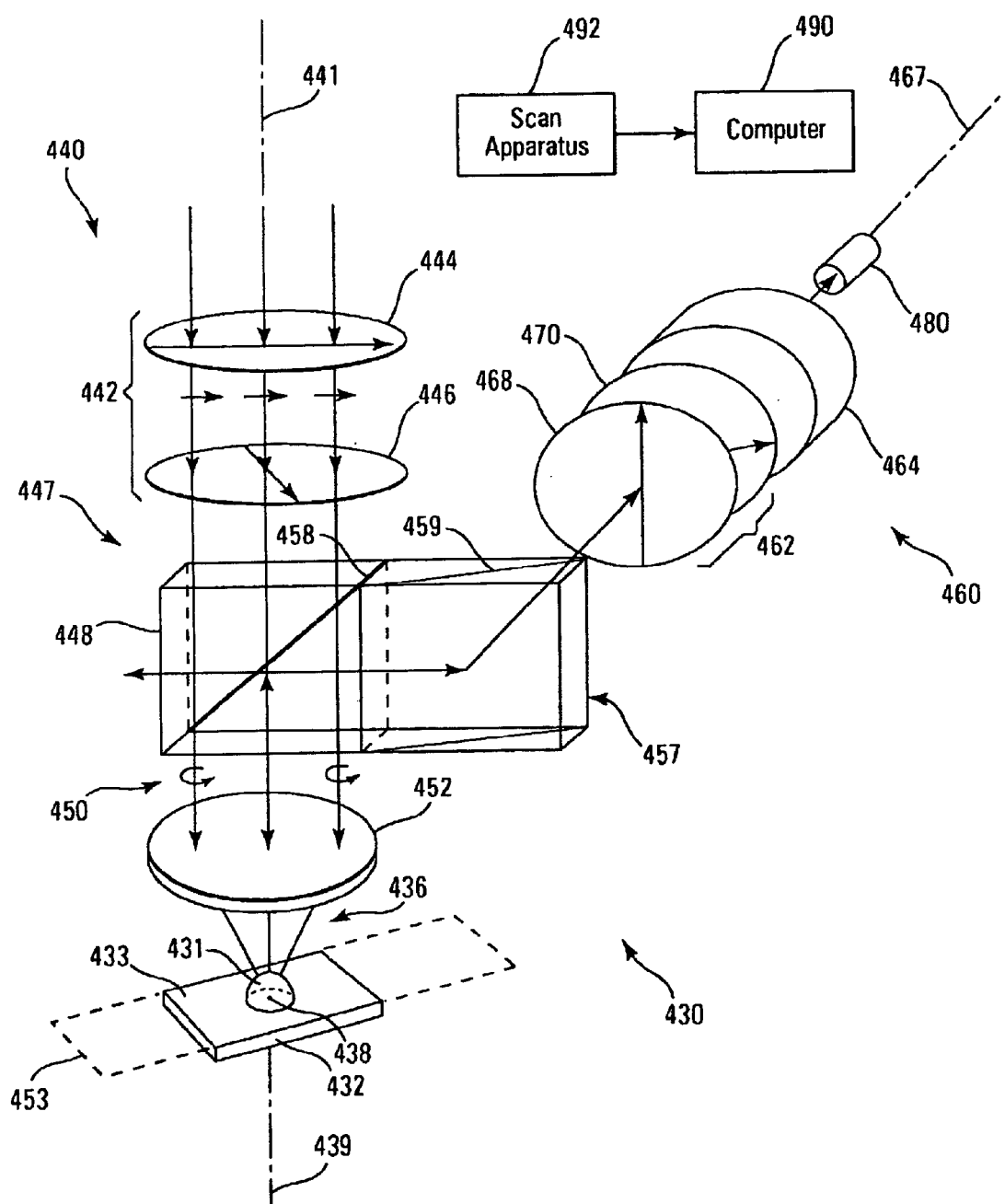
FIG. 7 shows one illustrative diagram of an embodiment of the solid immersion tunneling ellipsometer system shown generally in FIG. 2, using radially symmetric light and a solid immersion lens, according to the present invention.

FIG. 7 shows one illustrative diagram of another embodiment of the solid immersion tunneling ellipsometer system 30 shown generally in FIG. 2. The ellipsometer configuration of FIG. 7 uses radially symmetric techniques and a solid immersion lens configuration.

Radially symmetric ellipsometer system 430 shown in FIG. 7 acts like a multi-channel conventional ellipsometer. Every individual channel located at a different angular location inside a common annular ring (along the axis of the light beam) looks identical to others except for a phase delay. Such symmetry inside this annular ring is referred to herein as radial symmetry. The interference between these channels forms a high numerical aperture cone of light at the sample plane and gives rise to high resolution. Using this design, ellipsometric signals for use in determining ellipsometric parameters such as a ($\Psi$, $\Delta$) pair corresponding to a small spot can be measured.

Generally, the radially symmetric ellipsometer apparatus 430 uses radial symmetry to provide very high resolution in the measuring of a very small spot 438, preferably, a spot having a diameter less than 1 micron, of a sample 432. An illumination apparatus 440 provides radially symmetric polarized light incident normal to sample plane 433 of a sample 432. A beam splitter apparatus 447 directs the polarized light 450 to the objective lens 452. The objective lens 452 focuses the light onto a solid immersion lens 431, resulting in a focused spot 438 on the sample plane 433 which is located at the focal plane 453 of the objective lens 452. In other words, the sample plane 433 and the focal plane coincide. The sample plane 433 refers to a surface of the sample 436 to be analyzed (e.g., an ultrathin film). The incident light is normal to the sample plane 433, i.e., the incident plane of the light is normal to the sample plane 433. The sample 432 reflects at least a portion of the focused radially symmetric polarized light as radially symmetric elliptically polarized light. The reflected light is then used to generate a radially symmetric ellipsometer signal detectable for use in determining one or more characteristics of sample 432.

As shown in FIG. 7, the radially symmetric ellipsometer apparatus 430 includes the illumination apparatus 440, the beam splitter apparatus 447, the objective lens 452, and the solid immersion lens 431, all aligned along axis 439 for use in focusing radially symmetric polarized light to the spot 438 at the sample plane 433 of sample 432. As described above, the radially symmetric polarized light 450 is focused by an objective lens 452. The hemispherical solid-immersion lens (SIL) 431 is placed at the focal plane of the objective lens 433.

Figure 8:
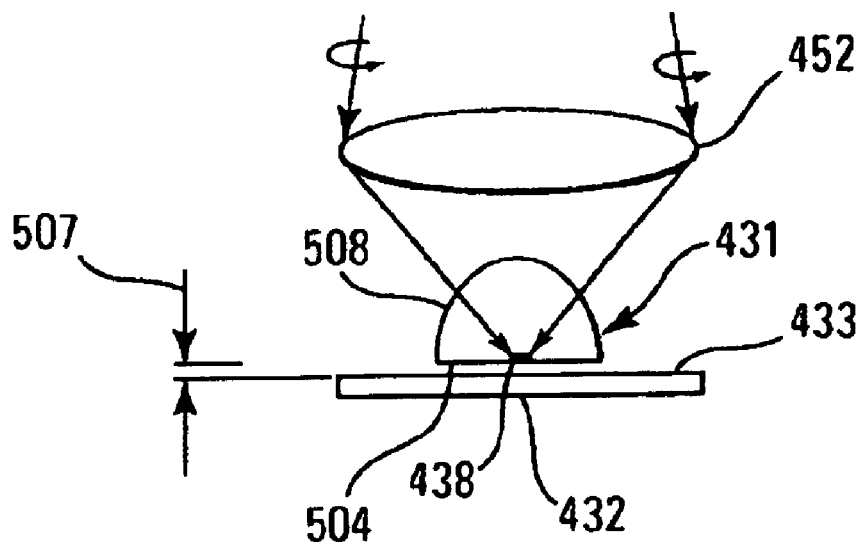
FIG. 8 shows a more detailed diagram of the solid immersion lens configuration of the ellipsometer system shown in FIG. 7.

The inclusion of a solid immersion lens 431 within ellipsometer apparatus 430 increases the resolution. Near field optics can be employed in the near field of the sample 432 to decrease the spot size of the ellipsometer apparatus 430 and provide tunneling according to the present invention. FIG. 8 is a more detailed diagram of the solid immersion apparatus including the solid immersion lens 431 shown in FIG. 7.

As shown in FIG. 8, the solid immersion lens (SIL) 431 may be positioned between the objective lens 452 and sample 432. Generally, the solid immersion lens 431 is a semispherical solid immersion lens, although other solid immersion lenses may be feasible with modifications to the apparatus 430. As shown in the embodiment of FIG. 8, the semispherical solid immersion lens 431 includes a lower surface 504 that is generally planar and an opposing surface having a radius (r) 508. Preferably, the radius 508 is in the range of several millimeters.

The lower surface 504 of the SIL is positioned adjacent the sample plane 433. The lower surface 504 may be positioned directly adjacent and in contact with the sample 432 at sample plane 433. However, the lower surface 504 may also be positioned with a space or gap 507 having a height (h) in a range of less than 10 nanometers between the sample plane 433 of the sample 432 and the lower surface 504 of the solid immersion lens 431.

The solid immersion lens 431 is generally formed of a material having a high index of refraction. Preferably, the refraction index may be in the range of 2 to 4. For example, the solid immersion lens 431 may be formed of GaP that has an index of refraction of about 3.5.

The light illuminating the objective lens 452 is focused onto the bottom or lower surface 504 of the solid immersion lens 431. The light focused down to lower surface 504 forms a tight spot 438 thereon. The optical coupling between the light focused on the lower surface 504 of the solid immersion lens 431 and the sample 432 produces a reflection captured by objective lens 452. For example, the spot may be about 0.1 microns. The spot size depends, at least in part, on the wavelength used in the apparatus.

The presence of the SIL 431 provides higher spatial resolution and optical tunneling for ellipsometric measurement. The spherical surface of the SIL 431 matches the wave front of the focused incident beam. The incident beam is therefore focused to a very small spot at the bottom tunneling surface 504 of the SIL 431 and reflected back from the SIL/sample interface. Optical tunneling will occur for those rays that have incident angles greater than the critical angle of the solid immersion lens 431.

The light focused down to the small spot 438 is reflected from the sample 432 and back for collection by the objective lens 452. The SIL 431 provides incident rays at angles that are both greater than and less than the critical angle. The SIL placed adjacent to the sample also provides tunneling for the rays that are incident at greater than the critical angle. The polarization state of the incident light on sample 432 is modified by Fresnel reflection for those rays incident at an angle less than the critical angle, and is modified by tunneling for those rays incident at greater than the critical angle, to provide reflected radially symmetric elliptically polarized light that is provided via the beam splitter apparatus 447 to an analyzer apparatus 460 of the radially symmetric ellipsometer apparatus 430.

The analyzer apparatus 460 includes a pure polarization rotator 462, a radial analyzer 464, and a detector 480 aligned along optical axis 467 of the analyzer apparatus 460. The pure polarization rotator 462 maintains the radially symmetric nature of the reflected light representative of the spot 438 on sample 432, which is thereafter focused to the detector 480 by the radial analyzer 464. Through operation upon the reflected radially symmetric elliptically polarized light, e.g., rotation of a component of the pure polarization rotator 462, a radially symmetric ellipsometric signal is detected at the detector 480 from which at least one characteristic of the sample 432 may be determined. For example, an ellipsometric pair ($\psi$, $\Delta$) may be derived based on the detected signal at detector 480 using computer apparatus 490 electrically coupled thereto as further described herein.

The illumination apparatus 440 may be any illumination device suitable for providing radially symmetric polarized light incident normal to sample plane 433 and thus normal to objective lens 452 which is generally positioned in a parallel manner to sample plane 433. As used herein, radially symmetric polarized light includes, but is clearly not limited to, radially polarized light and circularly polarized light. Any illumination that is radially symmetric in terms of polarization state in the annular region relative to the axis 439 may be suitable for use according to the present invention.

As shown in FIG. 7, the illumination apparatus 440 includes a light source 441 and a circular polarizer apparatus 442. The circular polarizer apparatus 442 includes a polarizer 444 for linearly polarizing light provided by light source 441 and a quarter wave plate 446 for providing suitable polarization to achieve circularly polarized light incident on objective lens 452.

The light source 441 may be any suitable light source at any suitable wavelengths. With use of multiple wavelengths, spectroscopic information may also be obtainable via detection of reflected light and analysis by computer apparatus 490 of the spectrum attained for the multiple wavelengths. Preferably, the light source 441 provides collimated light incident on polarizer 444 of circular polarizer apparatus 442. More preferably, the light source 441 is a laser beam providing precise collimated light. For example, a collimated He—Ne laser may be used to provide the collimated light.

The linear polarizer 444 and quarter wave plate 446 provide circularly polarized light 450. The circularly polarized light 450 passes through a first beam splitter 448 of beam splitter apparatus 447 and is incident on objective lens 452. The beam splitter 448 may introduce some polarization modification to the circularly polarized light provided by quarter wave plate 446. The linear polarizer 444 and quarter wave plate 446 are adjusted to pre-compensate for any such polarization modification introduced by the beam splitter 448. Therefore, the light 450 illuminating the objective lens 452 is circularly polarized such that radial symmetry is achieved in the illumination of sample 432.

Although radially polarized light may be used according to the present invention, preferably, the light incident on objective lens 452 is circularly polarized light. Therefore, with respect to the remainder of the description of this embodiment, the operation shall be described with respect to circularly polarized light.

The circularly polarized light 450 is focused by an objective lens 452. As described previously herein, the hemispherical solid-immersion lens (SIL) 431 is placed at the focal plane of the objective lens 433. The objective lens 452, and the solid immersion lens 431, are all aligned along axis 439 for use in focusing radially symmetric polarized light to a spot 438 at the sample plane 433 of sample 432. The SIL 431 provides incident rays at angles that are both greater than and less than the critical angle. The SIL 431 placed adjacent to the sample 432 also provides tunneling for the rays that are incident at greater than the critical angle.

The circularly polarized light focused down to a small spot 438 on the sample 432 is then reflected there from, at least in part, as radially symmetric elliptically polarized light. The reflected radially symmetric elliptically polarized light is collected by the objective lens 452 and provided to beam splitter apparatus 447 wherefrom it is directed to the analyzer apparatus 460 of radially symmetric ellipsometer apparatus 430.

The objective lens 452 is preferably a high numerical aperture objective lens. Preferably, the objective lens 452 has a numerical aperture in the range of 0.5 to less than 1.0. More preferably, the objective lens 452 has a numerical aperture in the range of 0.8 to less than 1.0. Preferably, for example, the spot 438 is generally of a size falling in the range of 0.25 to 0.5 microns. The size depends, at least in part, on the wavelength of the illumination source.

The reflected light collected by the objective lens 452 is provided to the analyzer apparatus 460 of the ellipsometer apparatus 430 by reflection in beam splitter apparatus 447. Beam splitter apparatus 447 comprises the first beam splitter 448 which passes the circularly polarized light from quarter wave plate 446 to the objective lens 452 for focusing upon the sample 432, and which provides for reflection and diversion of the reflected elliptically polarized light to analyzer apparatus 460. However, typically, the amplitude reflectivities of the two polarization states, $r_p$ and $r_s$, from a beam splitter such as first beam splitter 448, are different in amplitude and phase. As such, the reflected light will generally pick up some additional ellipticity from the reflection on the beam splitter interface 458 when diverted to analyzer apparatus 460. The amount of this additional ellipticity varies for different incident polarizations. To compensate for such added ellipticity, an identical additional beam splitter 457 is used, as shown in FIG. 7. The additional beam splitter 457 is identical to the beam splitter 448 but rotated in position to provide for such compensation.

Therefore, beam splitter apparatus 447 includes both first beam splitter 448 and second beam splitter 457. First beam splitter 448 includes an interface 458 for reflection of light collected by objective lens 452 normal to the plane of incident light from illumination apparatus 440, i.e., normal to the optical axis 439. The second beam splitter 457 includes an interface 459 for reflection of the diverted light from interface 458 of first beam splitter 448. The reflected light is diverted by the second beam splitter 457 such that the reflected light's direction is orthogonal to the light diverted from interface 458 and also orthogonal to the direction of light from illumination apparatus 440 which is incident on objective lens 452. As such, the s-component for the first beam splitter 448 becomes the p-component for the second beam splitter 457. Similarly, the p-component for the first beam splitter 448 changes into the s-component for the second beam splitter 457. As a result, the combination of these two beam splitters 448,457 has the same response to s- and p-components as the reflected light collected at the objective lens 452. As such, the polarization of the incident beam is maintained in the reflected light diverted to the analyzer apparatus 460.

The reflected radially symmetric elliptically polarized light provided to the analyzer apparatus 460 is operated upon by the pure polarization rotator 462 and the radial analyzer 464 such that a radially symmetric ellipsometric light is provided for detection by detector 480 for use in determining a characteristic of sample 432. The pure polarization rotator 462 is an angularly independent polarization rotator. In one illustrative embodiment, the pure polarization rotator 462 includes two half-wave plates 468 and 470.

With rotation of at least one of the half wave plates 468, 470 and with use of the radially symmetric analyzer 464 as described below, radially symmetric ellipsometric light is provided for detection by detector 480. The reflected intermediate elliptically polarized light provided from the pure polarization rotator 462 to the radial symmetric analyzer 464 is still radially symmetric and must be maintained in such a fashion by radially symmetric analyzer 464.

As described above, the radial analyzer 464 of the radially symmetric ellipsometer apparatus 430 must maintain the radial symmetry of the reflected radially symmetric elliptically polarized light. In other words, if one looks at this ellipsometer apparatus 430 as a multiple channel ellipsometer, every channel located at different angular locations inside a common annular region of the radial analyzer must look identical to the others except for phase delay.

Detector 480 of analyzer apparatus 460 is a photo detection device such as one or more photodiodes. Further, the detector 480 may be a charge coupled device detector (CCD). Any suitable detector for detecting the intensity of light and providing a signal representative thereof may be used according to the present invention. As described herein with reference to FIG. 6, the detector may be used to only detect reflected light only corresponding to the light provided incident at an angle greater than the critical angle, both greater than and less than the critical angle either separately or together, or a spatial filter may be used to obtain a suitable signal corresponding to an applicable event (e.g., incident light greater than or less than the critical angle).

With further reference to FIG. 7, the computer apparatus 490 runs software that allows the user to control the ellipsometer apparatus 430 by means of a graphical user interface (not shown) and is generally used to control the ellipsometer apparatus 430 and perform digital processing with respect to the ellipsometer signals provided thereto, e.g., by detector 480. For example, the computer apparatus 490 may be used to control rotation of any of the components described herein (e.g., rotation of a half wave plate in the pure polarization rotator 462), may be used to control application of the voltages to various components, may be used to deduce ellipsometric pairs for the signal detected by detector 480 of ellipsometer apparatus 430, or control any other components of the apparatus 430 interfaced to the computer, such as any microcontrollers, scanning apparatus 492, etc. For example, as described above, the spot 438 can be scanned under control of the computer apparatus 490 to produce polarization information with respect to multiple spots. Such multiple spot information may be used by the computer apparatus 490 to generate a mapped image.

Further, computer apparatus 490 includes software for providing data visualization and analysis capabilities via user control. For example, graphical illustrations of the thickness of a thin layer of sample 432 may be shown graphically after digital processing of any number of spots 438. In addition, spectroscopic information may be available upon use of any number of different wavelengths, as would be known to one skilled in the art.

In one illustrative manner of determining thickness and index of refraction using an ellipsometric pair ($\psi$, $\Delta$), computer apparatus 490 includes memory having a look-up table relating the ellipsometric pairs to thickness and index of refraction. For example, a computer program may be used to generate the $\psi$ and $\Delta$ model trajectories for various indexes of refraction and thickness. These results are stored in a look-up table in the computer memory of computer apparatus 490. When ellipsometric parameters are measured for a sample 432, the computer apparatus 490 may search the look-up table and do an interpolation and regression computation to find a corresponding index of refraction (n) and thickness (t). Further, alternatively, multi-variable regression analysis may be used in determining such parameters.

Radial symmetry, as used herein, refers to the symmetry inside an annular region of the ellipsometer apparatus 430 about a particular axis thereof. For example, in the provision of light incident on the objective lens 452, the radially symmetric polarized light from illumination apparatus 440 is radially symmetric about optical axis 439. Likewise, reflected light provided to the analyzer apparatus 460 is radially symmetric about optical axis 467. To be radially symmetric, the optical response of every different angular location within the annular region relative to the axis, e.g., axis 439 and axis 467, is identical to the optical responses of the other angular locations except for phase delay.

As indicated previously, the radial symmetry according to the present invention may be thought of in terms of a multiple channel apparatus. In other words, multiple channels parallel to the axes, e.g., axis 439 and axis 467, can be envisioned. Every individual channel located at different angular locations inside a common annular region looks identical to all the others except for phase delay.

Also as previously indicated, in the focusing of incident light onto the sample 432 by the combination of the objective lens 452 and the SIL 431, the interference between these channels forms a high numerical aperture cone of light 436 (with the use of the numerical aperture objective lens 452, e.g., a high numerical aperture objective lens) at the sample plane 433. Such radial symmetry and focusing of such radially symmetric light to the sample plane 433 gives rise to the high resolution of the present apparatus 430. Using the reflected light from the sample 432, the ellipsometric pair ($\psi$, $\Delta$) corresponding to a small spot 438 (where, as known to those skilled in the art, tan($\psi$) is the ratio of magnitudes of the reflection coefficients for the p-wave and s-wave, and $\Delta$ is the phase difference between the reflection coefficients of the p-wave and s-wave) can be measured. One or more characteristics of the sample 432, e.g., thickness or index of refraction, may then be deduced.

The radially symmetric techniques described herein are illustrated by FIG. 7, and are further described in U.S. application Ser. No. 09/691,346 that is incorporated by reference herein. However, FIG. 7 is only illustrative of one exemplary embodiment of a radially symmetric ellipsometer apparatus 430 according to the present invention. One will recognize that various components thereof may be modified without changing the radially symmetric nature of the ellipsometer apparatus 430.

Figure 9:
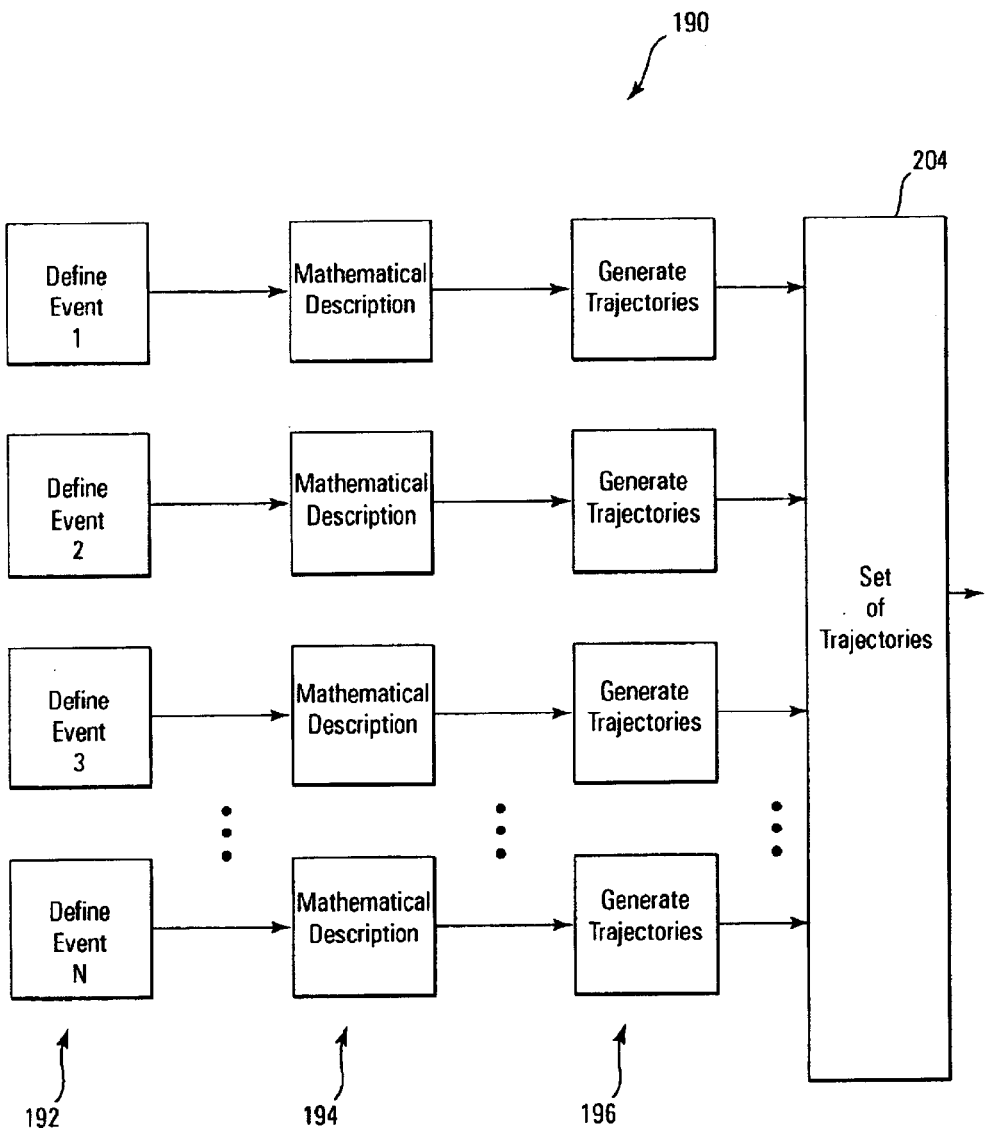
FIG. 9 is a processing flow diagram illustrating one embodiment of a portion of the general flow of processing to generate trajectories for use in the processing apparatus of the system such as shown generally in FIG. 2.

FIG. 9 is diagram of a processing flow 190 illustrating one embodiment of a portion of the general process flow shown generally in FIG. 2, primarily for use in generating trajectories. The process flow 190 is used to create a set of model trajectories 204 (or other relational information) that can be used along with specific measurement results (e.g., measured ellipsometric parameters) to determine one or more sample characteristic(s). Each type of measurement event 192 is defined in detail to create corresponding mathematical descriptions 194. Using the mathematical expressions 194 for a corresponding event 192, model trajectories are generated for that event (blocks 196). For example, events may include light incident at greater than the critical angle, light incident at less than the critical angle, and further, for example, a relationship between a structure parameter and one or more ellipsometric parameters (e.g., sidewall slope of a line structure related to the ellipsometric parameters).

For example, in one embodiment, each event relationship can be described using a mathematical expression whereby the desired sample characteristic is a function of $\Psi$ and $\Delta$, along with any other necessary parameters. For each event and from the mathematical description, trajectories are made that relate a measured ($\Psi$, $\Delta$) value to the value of the desired sample characteristic. In some cases, an event has many trajectories that are created by iterating some parameter of the event, for example, the angle of incidence.

The accuracy of determining one or more characteristics of the sample is very dependent on the use of a model that accurately represents the measurement event and the measurement system.

Figure 10:
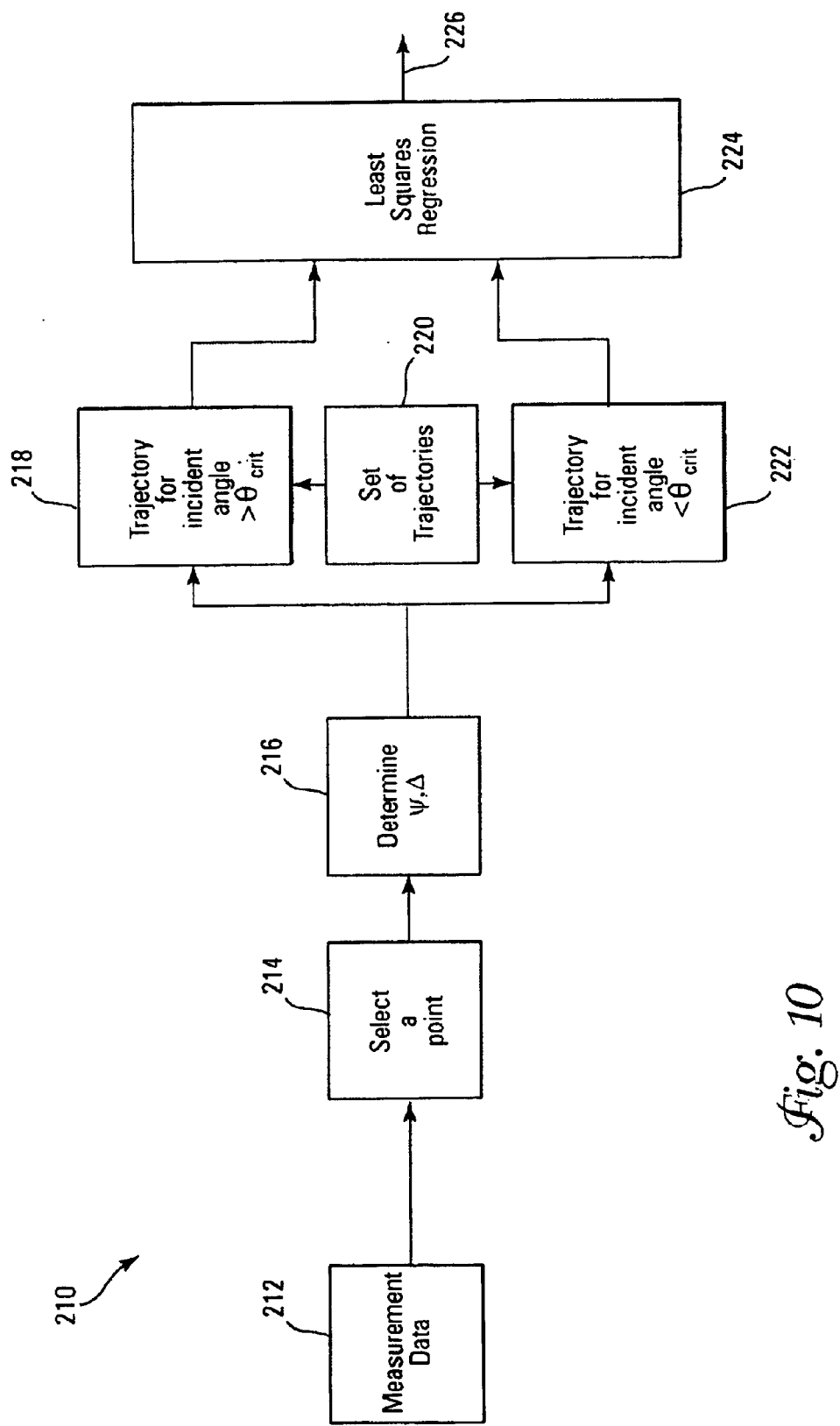
FIG. 10 is a processing flow diagram illustrating one embodiment of a portion of the general flow of processing shown generally in FIG. 5, to determine at least one characteristic of a sample (e.g., thickness of an ultrathin film).

FIG. 10 is a diagram of a processing flow 210 illustrating one embodiment of a portion of the general flow of processing shown generally in FIG. 5, to determine at least one characteristic of the sample. The processing flow may use one or more sets of trajectories or other relational information generated as described with reference to FIG. 9.

The process flow 210 shown in FIG. 10 may be used with single or multiple measurements made by an ellipsometry apparatus such as shown generally in FIG. 2 resulting in ellipsometric signals (i.e., measured data 212). From the measurement data 212, a point is selected 214, and ($\psi$, $\Delta$) pair is determined (block 216). Next, the ($\psi$, $\Delta$) pair is processed depending on the relationship of the angle of incidence for the light for which the (ψ, Δ) pair is determined to the critical angle of the solid immersion apparatus (e.g., critical angle of SIL or prism).

If the angle of incidence is greater than the critical angle, an appropriate trajectory is selected (block 218) from the set of model trajectories 220, and a fit by regression analysis (block 218) is done with the (ψ, Δ) pair determined for the light at greater than the critical angle, and the selected trajectory. This results in at least one sample characteristic being determined. In the case of a single measurement, no least squares regression 224 is required and the result is output 226.

If there is more than one measurement, the process is repeated, and another value for the at least one sample characteristic is determined in block 218. These steps are repeated for each measurement. The resulting set of values of at least one sample characteristic are then processed through a least squares regression 224, from which an optimized value of at least one sample characteristic is the result and output 226.

The present invention includes a technique that further improves the accuracy of results. This technique involves weighting the parameters during the regression analysis as is further described herein.

The procedure is similar for determining at least one sample characteristic when the incident light is at an angle less than the critical angle. If the angle of incidence is less than the critical angle, an appropriate trajectory is selected (block 222) from the set of model trajectories 220, and a fit by regression analysis (block 222) is done with the (ψ, Δ) pair determined for the light at less than the critical angle, and the selected trajectory. This results in at least one sample characteristic being determined. In the case of a single measurement, no least squares regression 224 is required and the result is output 226.

If there is more than one measurement, the process is repeated, and another value for the at least one sample characteristic is determined in block 222. These steps are repeated for each measurement. The resulting set of values of at least one sample characteristic are then processed through a least squares regression 224, from which an optimized value of at least one sample characteristic is the result and output 226.

Whenever the flow in FIG. 10 includes more than one measurement, the least squares regression step is performed, to optimize across all measurements. The merit functions previously described may be used to optimize the least squares fit. For the flow in FIG. 10, either of the previously mentioned merit functions (Merit Function 1 or Merit Function 2) may be applicable. Merit Function 1 is useable in any scenario where there are multiple measurements. Merit Function 2, which provides improved regression analysis, is applicable to FIG. 10 provided that there is at least one measurement from greater than the critical angle of the solid immersion apparatus and at least one measurement from less than the critical angle of the solid immersion apparatus. Merit Function 2 is a subset of Merit Function 1 as described herein.

Examination of the (ψ, Δ) trajectories of ultrathin films reveals a complementary feature between tunneling ellipsometry and conventional ellipsometry. While the ψ resolution is worse for conventional ellipsometry than for tunneling ellipsometry, the Δ resolution is usually better due to the multiple reflections, which are absent in the tunneling case. Thus, if one utilizes Δ values only from measurements for lower than the critical angle, and ψ values only for measurements from greater than the critical angle; the regression is generally more immune to noise. This technique is accomplished by weighting the ψ and Δ parameters during the regression analysis.

Figure 11:
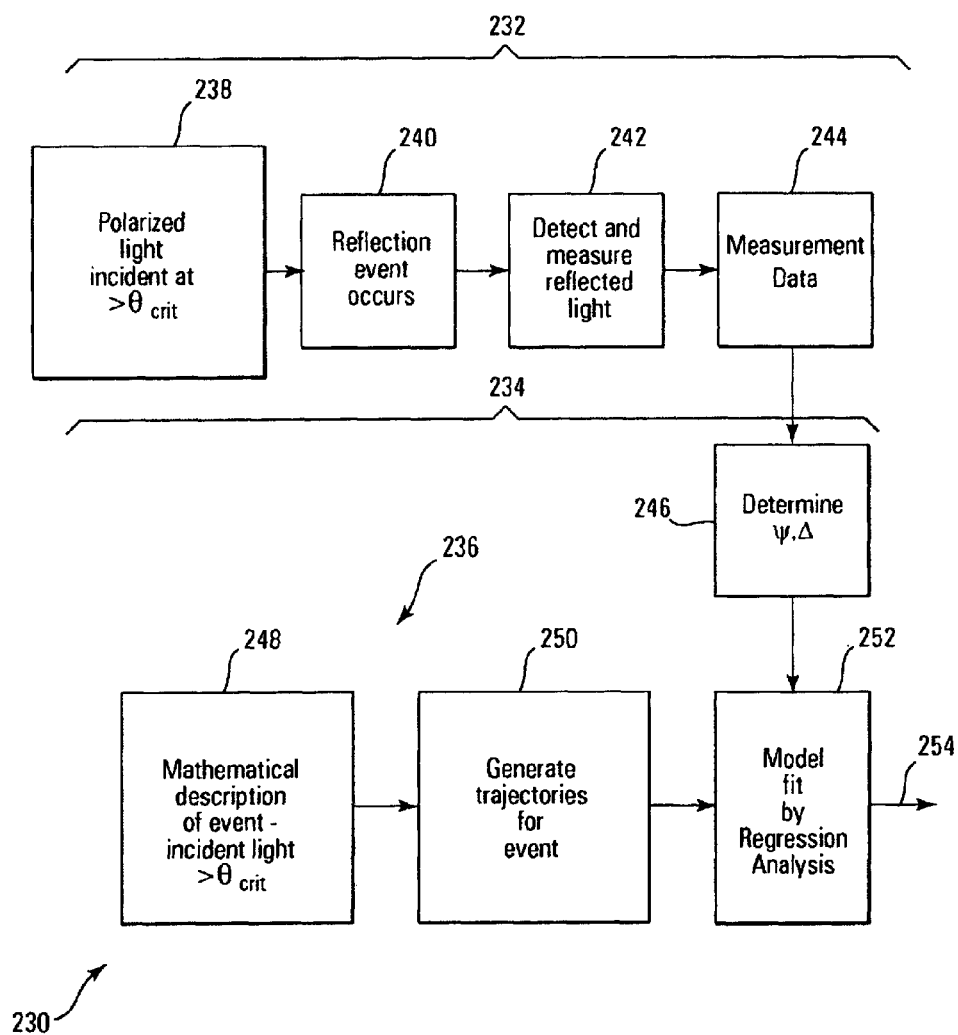
FIG. 11 is a processing flow diagram illustrating one embodiment of a portion of the general flow of processing shown generally in FIG. 5, where one model associated with incident light greater than the critical angle is used.

FIG. 11 is a diagram of a process flow 230 illustrating one embodiment of a portion of the general flow of processing shown generally in FIG. 4, where one model is used that describes the relationship between the ellipsometric parameters and at least one sample characteristic for ultrathin films. The processing flow 230 shown in FIG. 11 generally includes the physical measurement flow 232 and the computer processing flow 234.

Physical measurement flow 232 provides a general illustration of the operation of the ellipsometer measurement apparatus 32 shown generally in FIG. 2. One embodiment of the sequence of events of the ellipsometer apparatus 32 includes providing polarized light incident on the sample at an angle greater than the critical angle 238. The polarized light is then reflected from the sample 240. The reflected light is analyzed and detected 242. The physical measurement flow must include a method to selectively measure only reflected light corresponding to those rays that are incident at greater than the critical angle. For example, the measurement apparatus could include a filter mechanism to block the incident light corresponding to light at less than the critical angle, or a detector embodiment which implements an array of detectors, whereby the light measured from the detectors corresponding to the input rays at greater than the critical angle are used. Further, ring light detectors may also be used to detect the reflected light corresponding to incident light provided at greater than the critical angle. The measurement data 244 is provided as ellipsometric signals to the computer processing flow 234.

The computer processing flow 234 includes determining a (ψ, Δ) pair (block 246), providing models 236 and performing a model fit of the determined ellipsometric parameters (block 252) to deduce at least one characteristic 254 of the sample. The providing of the model (block 236), in one embodiment, includes mathematical description process 248 and generate trajectories process 250. Such processes have been defined generally above. Although various details are provided herein with regard to the generation of the models, any model no matter how generated that provides the suitable relationship between the sample characteristic or characteristics to be determined (e.g., thickness) and the ellipsometric parameters can be used. A regression analysis 252 is performed by fitting the (ψ, Δ) pair to a selected model trajectory of the model, thereby producing the result (i.e., at least one characteristic of the sample). The method of the present invention supports a variable number of events and event types (and therefore, model types).

The processing flow diagram shown in FIG. 11 specifically describes the process for the case where the incident light is incident at an angle greater than the critical angle (block 238). The process for the case where the light is incident at an angle less than the critical angle is similar, with the following differences: first, block 238 would be provide polarized light at an incident angle less than the critical angle; second, there would be a mechanism so that the reflected light that was analyzed and detected would only be the reflected light from the incident rays at less than the critical angle; and third, the provide model block 236 would describe and generate trajectories for an event where the light was incident at an angle less than the critical angle.

Figure 12:
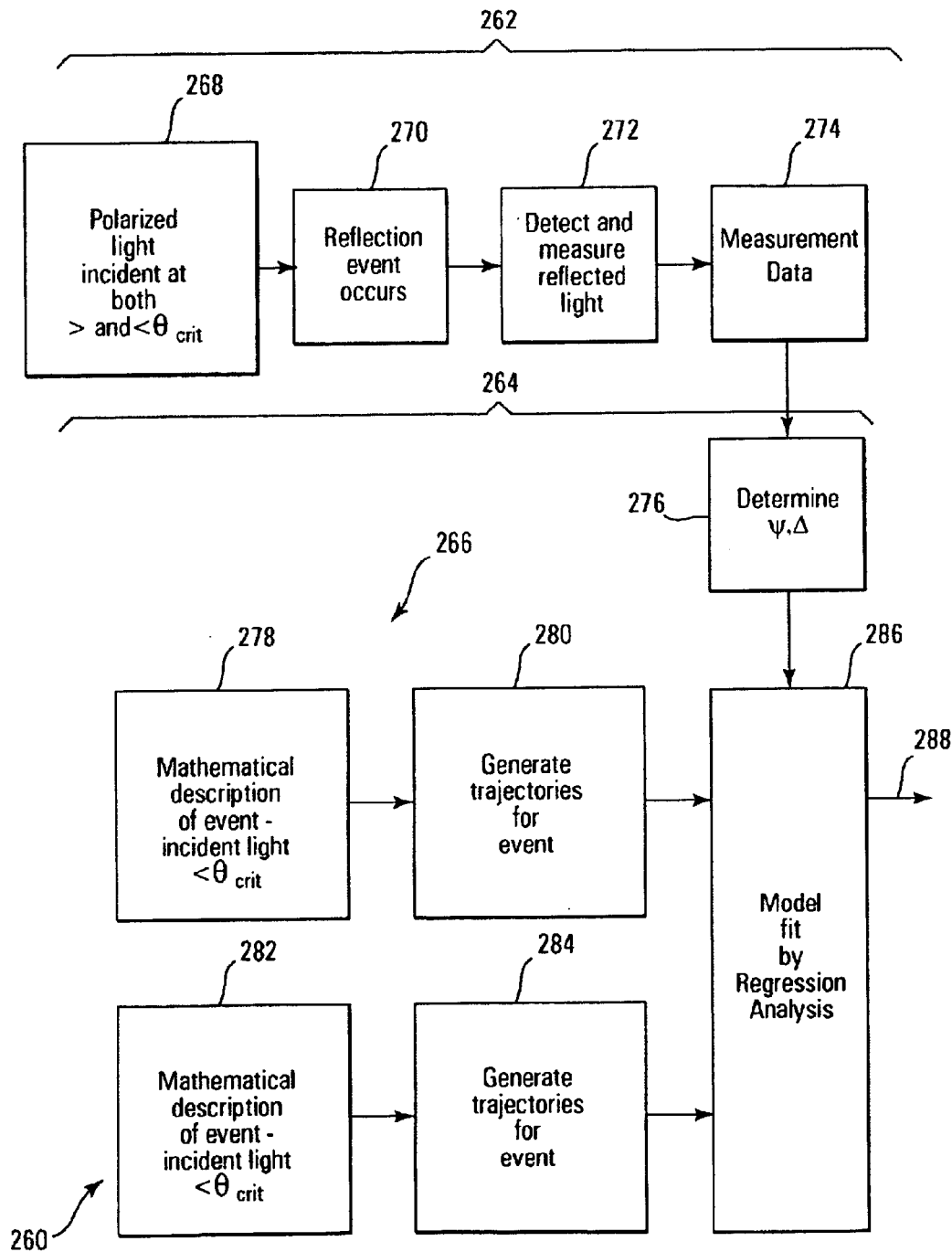
FIG. 12 is a processing flow diagram illustrating one embodiment of a portion of the general flow of processing shown generally in FIG. 5, where two models associated with incident light greater than the critical angle and less than the critical angle are used.

Whenever the flow in FIG. 11 includes more than one measurement, the least squares regression step is performed, to optimize across all measurements. For the flow in FIG. 11, Merit Function 1 can be used since there is only one model, and therefore, all the measurements are performed either with incident light greater than the critical angle of the solid immersion apparatus, or with incident light less than the critical angle of the solid immersion apparatus. FIG. 12 is another processing flow diagram 260 illustrating one embodiment of a portion of the general flow of processing shown generally in FIG. 2. In this case, a combination of two models is used; one for angles greater than the critical angle and one for angles less than the critical angle.

The overall process flow 260 includes a physical measurement flow 262 and a computer processing flow 264. Physical measurement flow 262 provides a general illustration of the operation of the ellipsometer measurement apparatus 32 such as shown generally in FIG. 2. One embodiment of the sequence of events of the ellipsometer apparatus 32 includes providing polarized light incident on the sample at both an angle greater than the critical angle and an angle less than the critical angle 268. The polarized light is then reflected from the sample 270. The reflected light is analyzed and detected 272.

The physical measurement flow 262 must include a method to discriminate between the light corresponding to those rays that are incident at greater than the critical angle, and the light corresponding to those rays that are incident at an angle less than the critical angle. For example, the measurement apparatus could include a filter mechanism like that described herein to allow certain light corresponding to light at less than the critical angle and greater than the critical angle to pass to the detector, or a detector embodiment which implements an array of detectors, whereby the light measured from the detectors corresponding to the input rays at greater than and less than the critical angle are detected. Further, the method may include any other physical or process oriented vehicle for providing such separation between greater than critical angle and less than critical angle information. The measurement data 274 is provided as ellipsometric signals to the computer processing flow 264.

The computer processing flow 264 includes determining the ($\psi$, $\Delta$) pair 276, creating models 266, and performing a fit of the data to the model 286, to produce the result (e.g., at least one characteristic of the sample 288). The providing model block 266, in one embodiment, includes mathematical description process 278 and generate trajectories process 280 which creates a set of trajectories (or other relational information) for the event in which the light is incident at an angle greater than the critical angle. The providing model block 266 further includes, in one embodiment, another mathematical description process 282 and generate trajectories process 284 which creates a set of trajectories (or other relational information) for the event in which the light is incident at an angle less than the critical angle.

Although various details are provided herein with regard to the generation of the models, any model no matter how generated that provides the suitable relationship between the sample characteristic or characteristics to be determined (e.g., thickness) and the ellipsometric parameters can be used.

A regression analysis 286 is performed by fitting the measured ($\psi$, $\Delta$) pair (e.g., determined in block 276) to the selected model trajectory of the model, thereby producing the result 288 (i.e., at least one characteristic of the sample). The model fit by regression analysis (block 286) performs a fit of the measured ($\psi$, $\Delta$) (e.g., determined in block 276) to a trajectory which is either 280 if the measured ($\psi$, $\Delta$) corresponds to light incident at greater than the critical angle, or trajectory 284 if the measured ($\psi$, $\Delta$) corresponds to light incident at less than the critical angle.

For any particular measurement taken, the measurement data must be associated with the correct and compatible model/trajectory. Also, one must choose a model that is appropriate for the specific physical system that is being measured. For example, one must choose different models for the case of a single thin film (of thickness and index of refraction to be determined) on a given substrate and the case of multiple thin films on a substrate. With multiple models, the regression analysis 286 may include an additional step of performing a least squares fit on all the generated results to optimize the results.

Whenever the flow in FIG. 12 includes more than one measurement, the least squares regression step is performed, to optimize across all measurements. The merit functions previously described are used to optimize the least squares fit. For the flow in FIG. 12, either of the previously mentioned merit functions (Merit Function 1 or Merit Function 2) may be applicable. Merit Function 1 is useable in any scenario where there are multiple measurements. Merit Function 2, which provides improved regression analysis, is a subset of Merit Function 1, as previously stated herein.

The methods and apparatus of the present invention may also include a spatially resolved ellipsometry system providing the capability to determine critical characteristics of a structure, such as the characterization of a sidewall shape of a line formed on a substrate. The response of sub-wavelength structures, for example, lines on integrated circuits, to incident light is polarization dependent. Numerical simulation and experimental results have shown that the polarization effect depends on the shape of the structure, for example, the sidewall shape. In the present invention, one can use spatially resolved ellipsometry to extract ellipsometric information from the corresponding line structures, to determine the sidewall shape, such as undercutting and sidewall slope. Since the line structures are smaller than the wavelength, a vector diffraction model that solves Maxwell's equations rigorously is required, and the focused beam rigorous coupled wave analysis (FB-RCWA) is utilized.

The present invention includes a modeling process to create a model including at least trajectories that show the relationship between ellipsometric parameters and desired sample characteristics (e.g., slope). The present invention, in one embodiment, includes a model for sidewall slope measurement of a line on a substrate, as a function of the ellipsometric parameters.

Figure 13B:
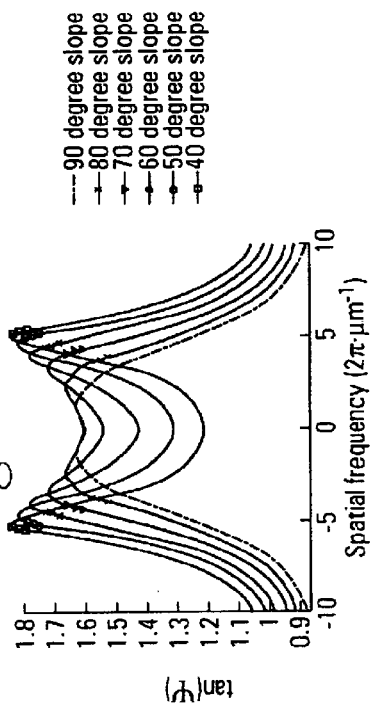
FIGS. 13A, 13B, 13C, and 13D show a setup and associated trajectories for illustrating the use of ellipsometric measurements in the determination of the sidewall shape of a line.
Figure 13D:
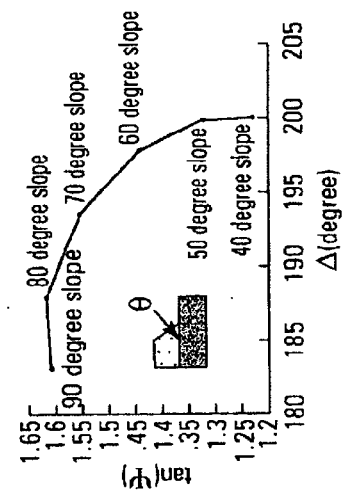
Figure 13A:
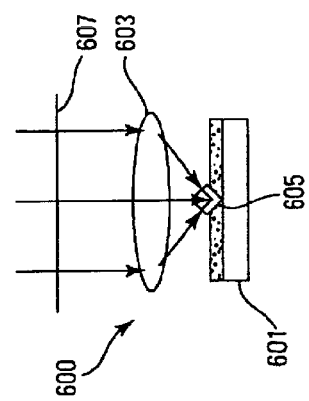

An ellipsometric apparatus 600 is shown in FIG. 13A for use in providing ellipsometric signals to determine one or more ellipsometric parameters (e.g., ($\psi$, $\Delta$)). However, any ellipsometric signals described herein or elsewhere may be suitable for providing ellipsometric data for determining ellipsometric parameters (e.g., ($\psi$, $\Delta$)).

In this one illustration, sample 601 is illuminated by a Gaussian beam focused by a microscope objective 603 (NA=0.8). When the beam illuminates the trench 605, the reflected elliptically polarized light is analyzed and detected to provide ellipsometric signals. With ellipsometric signals provided, ellipsometric parameters can be determined. By using a suitable model and trajectories showing the relationship between slope of a wall of the trench and the ellipsometric parameters, one can determine slope of the wall. In this case, we can determine the sidewall slope of the trench without actually resolving its shape.

Figure 13C:
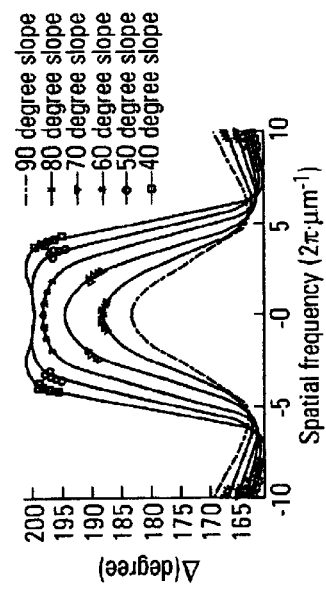

FIGS. 13B and 13C show the trajectories created using a model of this event, i.e., measuring the sidewall slope of a line structure. Such trajectories for different slopes have enough separation to allow for accurate results when fitting ellipsometric parameters to the model. FIG. 13B illustrates the magnitude ratio (tan ψ) and FIG. 13C illustrates the phase delay (Δ) between two illumination conditions across the back focal plane 607 of the focusing lens 603. The curves for different sidewall slopes are different. The sidewall shape can be distinguished by measuring the state of polarization of one or more rays that correspond to different spatial frequencies at the back of the focal plane 607. FIG. 13D depicts the (tan ψ, Δ) trajectory that corresponds to measurement by the on-axis ray.

Note that the ellipsometric apparatus used to carry out the measurements as shown in FIG. 13A is just an example, and that any ellipsometric apparatus, including those described in the present invention, could be used.

It will be recognized that one or more elements or processes described with reference to certain embodiments may be used with other embodiments described herein as well. For example, the use of the merit function for regression analysis described with reference to FIGS. 3 and 4 may be used in the regression analysis described with reference to FIG. 10. Further, for example, the type of detector or SIL used in one embodiment of an ellipsometer apparatus may be used for other apparatus described herein as well.

All references cited herein are incorporated in their entirety as if each were incorporated separately. This invention has been described with reference to illustrative embodiments and is not meant to be construed in a limiting sense. Various modifications of the illustrative embodiments, as well as additional embodiments of the invention, will be apparent to persons skilled in the art upon reference to this description.

What is claimed is:

1. An ellipsometry method comprising:
   receiving one or more ellipsometric signals corresponding to at least one ray of polarized light provided at an angle greater than a critical angle of a solid immersion apparatus, wherein the solid immersion apparatus comprises a surface located adjacent a thin film of a sample;
   determining one or more measured ellipsometric parameters as a function of the one or more ellipsometric signals for the at least one ray of the polarized light provided at an angle greater than the critical angle; and
   determining at least one characteristic of the thin film by fitting the one or more measured ellipsometric parameters to a model, wherein the model provides a relationship between the at least one characteristic for thin films and model ellipsometric parameters corresponding to the one or more measured ellipsometric parameters.

2. The method of claim 1, wherein the model provides a relationship between the at least one characteristic for thin films having a thickness less than 100 angstroms and model ellipsometric parameters corresponding to the one or more measured ellipsometric parameters.

3. The method of claim 1, wherein the solid immersion apparatus comprises one of a hemispheric lens and a stigmatic lens.

4. The method of claim 1, wherein the one or more measured ellipsometric parameters comprise ψ and Δ for the at least one ray of the polarized light provided at an angle greater than the critical angle.

5. The method of claim 1, wherein fitting the one or more measured ellipsometric parameters to a model comprises providing a greater weight to the measured ellipsometric parameter ψ than the measured ellipsometric parameter Δ when determining the at least one characteristic.

6. The method of claim 1, wherein the at least one characteristic comprises at least one of thickness and index of refraction of one or more thin films.

7. The method of claim 1, wherein the method further comprises:
   receiving one or more ellipsometric signals corresponding to at least one ray of polarized light provided at an angle less than the critical angle of the solid immersion apparatus; and
   determining one or more ellipsometric parameters as a function of the one or more ellipsometric signals for the at least one ray of the polarized light provided at an angle less than the critical angle, wherein the method further comprises determining at least one characteristic for the thin film based on one or more measured ellipsometric parameters determined for the at least one ray of the polarized light provided at an angle less than the critical angle and one or more measured ellipsometric parameters determined for the at least one ray of the polarized light provided at an angle less than the critical angle.

8. The method of claim 7, wherein determining the at least one characteristic for the thin film comprises:
   fitting the one or more measured ellipsometric parameters determined for the at least one ray of the polarized light provided at an angle greater than the critical angle to a model that provides a relationship between the at least one characteristic for thin films having a thickness less than 100 angstroms and model ellipsometric parameters corresponding to the one or more measured ellipsometric parameters;
   fitting the one or more measured ellipsometric parameters determined for the at least one ray of the polarized light provided at an angle less than the critical angle to a model that provides a relationship between the at least one characteristic for thin films of any thickness and model ellipsometric parameters corresponding to the one or more measured ellipsometric parameters; and
   determining the at least one characteristic using both the results of the model fitting of the one or more measured ellipsometric parameters determined for the at least one ray of the polarized light provided at an angle greater than the critical angle and of the one or more measured ellipsometric parameters determined for the at least one ray of the polarized light provided at an angle less than the critical angle.

9. The method of claim 8, wherein the one or more measured ellipsometric parameters comprise ψ and Δ for the at least one ray of the polarized light provided at an angle greater than the critical angle and for the at least one ray of the polarized light provided at an angle less than the critical angle.

10. The method of claim 9, wherein the at least one characteristic is determined using a fitting method utilizing only ψ values determined for the at least one ray of polarized light provided at an angle greater than the critical angle and Δ values determined for the at least one ray of polarized light provided at an angle less than the critical angle.

11. The method of claim 1, wherein the solid immersion apparatus comprises a prism, wherein the prism comprises the surface located adjacent the thin film of the sample and the critical angle.

12. The method of claim 1, wherein the solid immersion apparatus comprises an objective lens and a solid immersion lens, wherein the solid immersion lens comprises the surface located adjacent the thin film of the sample and the critical angle, and wherein the method further comprises:
   providing polarized light incident normal to the thin film of the sample;

focusing the polarized light on the solid immersion lens using the objective lens; and collecting elliptically polarized reflected light from the sample.

13. The method of claim 12, wherein providing the polarized light further comprises providing radially symmetric polarized light.

14. The method of claim 12, wherein the elliptically polarized light comprises at least elliptically polarized light corresponding to at least one ray of the polarized light provided at an angle greater than the critical angle of the solid immersion lens, and further wherein the method comprises detecting the elliptically polarized light resulting in one or more ellipsometric signals for use in determining one or more ellipsometric parameters for the at least one ray of the polarized light provided at an angle greater than the critical angle of the solid immersion lens.

15. The method of claim 12, wherein the surface of the solid immersion lens is adjacent the thin film but separated therefrom by a substrate upon which the thin film is provided, wherein the solid immersion lens comprises an abbreviated hemispheric lens, wherein the abbreviated hemispheric lens has a height less than a hemisphere, and further wherein the polarized light is incident on the thin film through the substrate.

16. The method of claim 1, wherein the surface of the solid immersion apparatus is separated from the sample by a distance.

17. The method of claim 1, wherein the surface of the solid immersion apparatus is positioned in contact with the sample.

18. An ellipsometer apparatus comprising:

an interface apparatus operable to receive one or more ellipsometric signals corresponding to at least one ray of polarized light provided at an angle greater than a critical angle of a solid immersion apparatus, the solid immersion apparatus comprising a surface adapted to be positioned adjacent a thin film of a sample; and a processing apparatus operable to:

determine one or more measured ellipsometric parameters as a function of the one or more ellipsometric signals for the at least one ray of the polarized light provided at an angle greater than the critical angle; and determine at least one characteristic of the thin film by fitting the one or more measured ellipsometric parameters to a model, wherein the model provides a relationship between the at least one characteristic for thin films and model ellipsometric parameters corresponding to the one or more measured ellipsometric parameters.

19. The apparatus of claim 18, wherein the model provides a relationship between the at least one characteristic for thin films having a thickness less than 100 angstroms and model ellipsometric parameters corresponding to the one or more measured ellipsometric parameters.

20. The apparatus of claim 18, wherein the one or more measured ellipsometric parameters comprise $\psi$ and $\Delta$ for the at least one ray of the polarized light provided at an angle greater than the critical angle.

21. The apparatus of claim 18, wherein the at least one characteristic comprises at least one of thickness and index of refraction of one or more films.

22. The apparatus of claim 18, wherein the interface apparatus is further operable to receive one or more ellipsometric signals corresponding to at least one ray of polarized light provided at an angle less than the critical angle of the solid immersion apparatus, and wherein the processing apparatus is further operable to:

determine one or more measured ellipsometric parameters as a function of the one or more ellipsometric signals for the at least one ray of the polarized light provided at an angle less than the critical angle; and determine at least one characteristic for the thin film based on one or more measured ellipsometric parameters determined for the at least one ray of the polarized light provided at an angle less than the critical angle and one or more ellipsometric parameters determined for the at least one ray of the polarized light provided at an angle less than the critical angle.

23. The apparatus of claim 22, wherein the processing apparatus is further operable, when determining the at least one characteristic for the thin film, to:

fit the one or more measured ellipsometric parameters determined for the at least one ray of the polarized light provided at an angle greater than the critical angle to a model that provides a relationship between the at least one characteristic for thin films less than 100 angstroms and model ellipsometric parameters corresponding to the one or more measured ellipsometric parameters;

fit the one or more measured ellipsometric parameters determined for the at least one ray of the polarized light provided at an angle less than the critical angle to a model that provides a relationship between the at least one characteristic for thin films of any thickness and model ellipsometric parameters corresponding to the one or more measured ellipsometric parameters; and determine the at least one characteristic using both the results of the model fitting of the one or more measured ellipsometric parameters determined for the at least one ray of the polarized light provided at an angle greater than the critical angle and the model fitting of the one or more measured ellipsometric parameters determined for the at least one ray of the polarized light provided at an angle less than the critical angle.

24. The apparatus of claim 23, wherein the one or more measured ellipsometric parameters comprise $\psi$ and $\Delta$ for the at least one ray of the polarized light provided at an angle greater than the critical angle and for the at least one ray of the polarized light provided at an angle less than the critical angle.

25. The apparatus of claim 18, wherein the solid immersion apparatus comprises a prism, wherein the prism comprises the surface adapted to be located adjacent the thin film of the sample and the critical angle.

26. The apparatus of claim 18, wherein the solid immersion apparatus comprises one of a hemispheric lens and a stigmatic lens.

27. The apparatus of claim 18, wherein the surface of the solid immersion apparatus is positioned in contact with the sample.

28. The apparatus of claim 18, wherein the surface of the solid immersion apparatus is separated from the sample by a distance.

29. The apparatus of claim 18, wherein the solid immersion apparatus comprises an objective lens and a solid immersion lens, wherein the solid immersion lens comprises the surface adapted to be located adjacent the thin film of the sample and the critical angle, and further wherein the apparatus comprises:

a light source to provide polarized light incident normal to the thin film of the sample, wherein the objective lens is adapted to focus the polarized light on the solid immersion lens and collect elliptically polarized reflected light from the sample; and a detector operable to detect the elliptically polarized light resulting in one or more ellipsometric signals for the at least one ray of the polarized light provided at an angle greater than the critical angle of the solid immersion lens.

30. The apparatus of claim 29, wherein the light source is operable to provide radially symmetric polarized light.

31. The apparatus of claim 29, wherein the surface of the solid immersion lens is adapted to be located adjacent the thin film but separated therefrom by a substrate upon which the thin film is provided, wherein the solid immersion lens comprises an abbreviated hemispheric lens, wherein the abbreviated hemispheric lens has a height less than a hemisphere, and further wherein the polarized light is incident on the thin film through the substrate.

* * * * *